United States Patent
Kato et al.

(10) Patent No.: US 12,249,066 B2
(45) Date of Patent: Mar. 11, 2025

(54) METHOD FOR LEARNING THRESHOLD VALUE

(71) Applicant: EIZO Corporation, Hakusan (JP)

(72) Inventors: Yu Kato, Hakusan (JP); Masafumi Higashi, Hakusan (JP); Reo Aoki, Hakusan (JP); Mamoru Ogaki, Hakusan (JP)

(73) Assignee: EIZO Corporation, Hakusan (JP)

( * ) Notice: Subject to any disclaimer, the term of this patent is extended or adjusted under 35 U.S.C. 154(b) by 458 days.

(21) Appl. No.: 17/622,493

(22) PCT Filed: Jul. 12, 2019

(86) PCT No.: PCT/JP2019/027709
§ 371 (c)(1),
(2) Date: Dec. 23, 2021

(87) PCT Pub. No.: WO2021/009804
PCT Pub. Date: Jan. 21, 2021

(65) Prior Publication Data
US 2022/0245806 A1    Aug. 4, 2022

(51) Int. Cl.
*G06V 10/75*    (2022.01)
*G06T 7/00*    (2017.01)
(Continued)

(52) U.S. Cl.
CPC .............. *G06T 7/0012* (2013.01); *G06T 7/62* (2017.01); *G06V 10/28* (2022.01); *G06V 10/50* (2022.01);
(Continued)

(58) Field of Classification Search
CPC .................................................. G06T 7/0012
See application file for complete search history.

(56) References Cited

U.S. PATENT DOCUMENTS

2019/0053789 A1* 2/2019 Malik ................. G06F 18/2411
2019/0057778 A1* 2/2019 Porter .................... G16H 50/50
(Continued)

FOREIGN PATENT DOCUMENTS

JP    6-195511 A    7/1994
JP    2002-51987 A    2/2002
(Continued)

OTHER PUBLICATIONS

International Search Report dated Sep. 10, 2019 in corresponding application PCT/JP2019/027709; 2 pages.
(Continued)

*Primary Examiner* — Di Xiao
(74) *Attorney, Agent, or Firm* — Maier & Maier, PLLC

(57) ABSTRACT

The present invention has been made in view of the foregoing, and an object thereof is to provide a method for learning a threshold that can provide a more objective threshold applied to pixels in the mammography image.
The present invention provides a method for learning a threshold value applied to pixels in a mammography image comprising: an acquiring step; and a learning step, wherein in the acquiring step, the mammography image is acquired, in the learning step, a relationship between the mammography image and a mammary gland pixel estimation threshold is learned, the mammary gland pixel estimation threshold is a threshold value used to calculate a mammary gland pixel area of each pixel of a mammary gland region in the mammography image, and the mammary gland pixel area is a value indicating a degree of a mammary gland pixel-likeness of the pixel in the mammography image.

6 Claims, 20 Drawing Sheets

(51) Int. Cl.
  *G06T 7/62*     (2017.01)
  *G06V 10/28*    (2022.01)
  *G06V 10/50*    (2022.01)
(52) U.S. Cl.
  CPC .. *G06V 10/758* (2022.01); *G06T 2207/20081* (2013.01); *G06T 2207/30068* (2013.01)

(56) References Cited

U.S. PATENT DOCUMENTS

2019/0304088 A1* 10/2019 Morita ................ A61B 5/0091
2020/0214658 A1   7/2020 Otomaru et al.

FOREIGN PATENT DOCUMENTS

| JP | 2015-167829 A | | 9/2015 | | |
|----|---------------|---|--------|---|---|
| JP | 2016-158963 A | | 9/2016 | | |
| JP | 2016-206693 A | | 12/2016 | | |
| JP | 2017051752 A | * | 3/2017 | ........... | A61B 6/0414 |
| JP | 2019-63504 A | | 4/2019 | | |
| WO | WO-2020019671 A1 | * | 1/2020 | ........... | G06T 7/0012 |

OTHER PUBLICATIONS

Jonathan Long, et al.; "Fully Convolutional Networks for Semantic Segmentation"; IEEE Transactions on Pattern Analysis and Machine Intelligence; vol. 39; Apr. 4, 2017; 10 pgs.

\* cited by examiner

MAMMARY GLAND
REGION MAP R

EACH PIXEL IN MAMMARY
GLAND REGION MAP

MAMMARY GLAND PIXEL AREA MAP

|      | 0.80 | 0.95 |      |
|------|------|------|------|
|      | 0.95 | 0.95 | 0.80 |
| 0.6  | 0.9  | 0.95 | 0.95 |
| 0.90 | 0.95 | 0.95 | 0.95 |
| 0.95 | 0.95 | 0.95 | 0.95 |
| 0.95 | 0.95 | 0.95 | 0.95 |
| 0.60 | 0.95 | 0.95 | 0.90 |
|      | 0.80 |      |      |

PIXEL VALUE Pv OF EACH PIXEL IN MAMMARY GLAND REGION

|     | 1 | 1 |   |
|-----|---|---|---|
|     | 1 | 1 | 1 |
| 0.1 | 1 | 1 | 1 |
| 1   | 1 | 1 | 1 |
| 1   | 1 | 1 | 1 |
| 1   | 1 | 1 | 1 |
| 0.1 | 1 | 1 | 1 |
|     | 1 |   |   |

MAMMARY GLAND PIXEL AREA La OF EACH PIXEL IN MAMMARY GLAND REGION

MAMMARY GLAND DENSITY = 100(%) × 24.2 / 26 = 93(%)

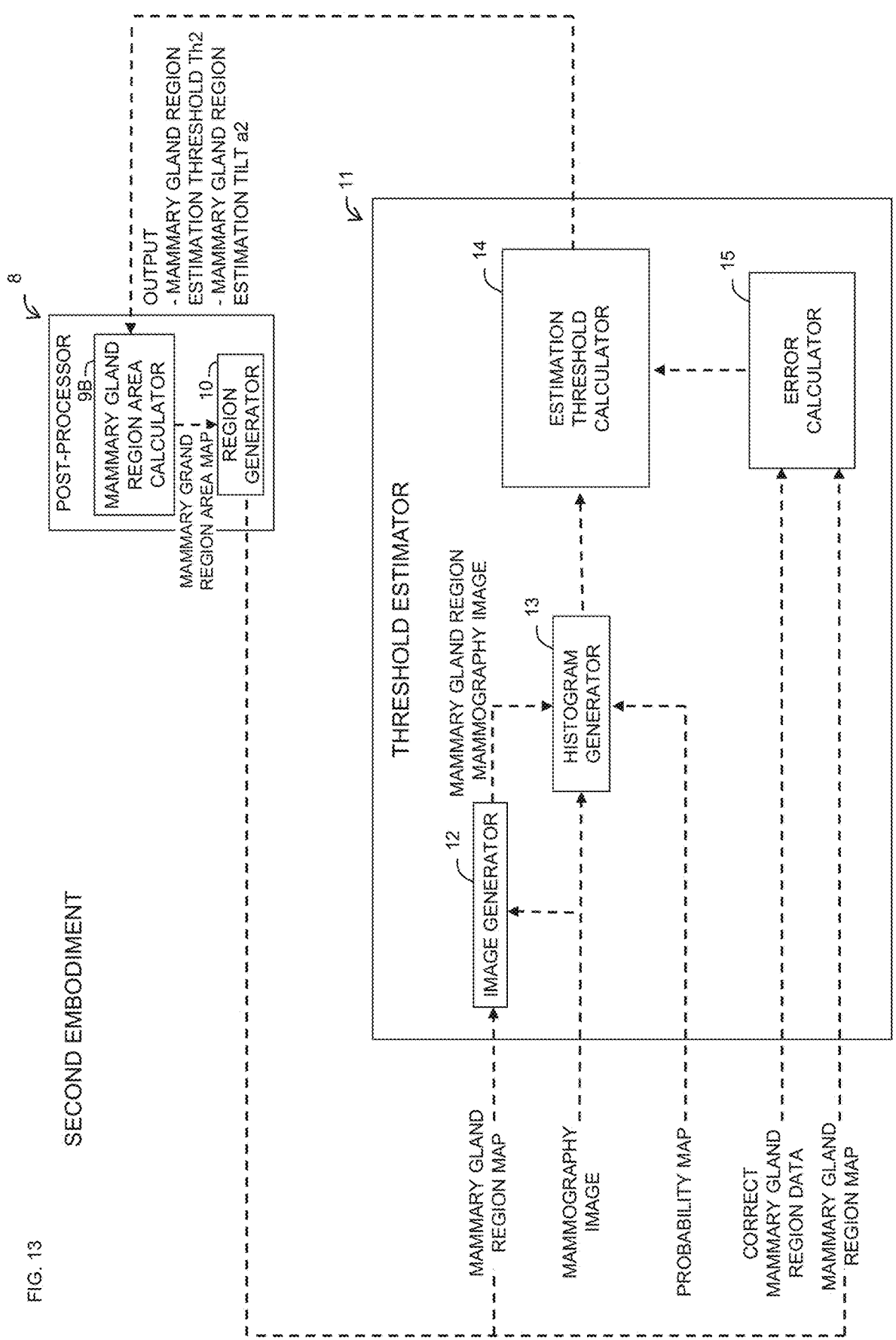

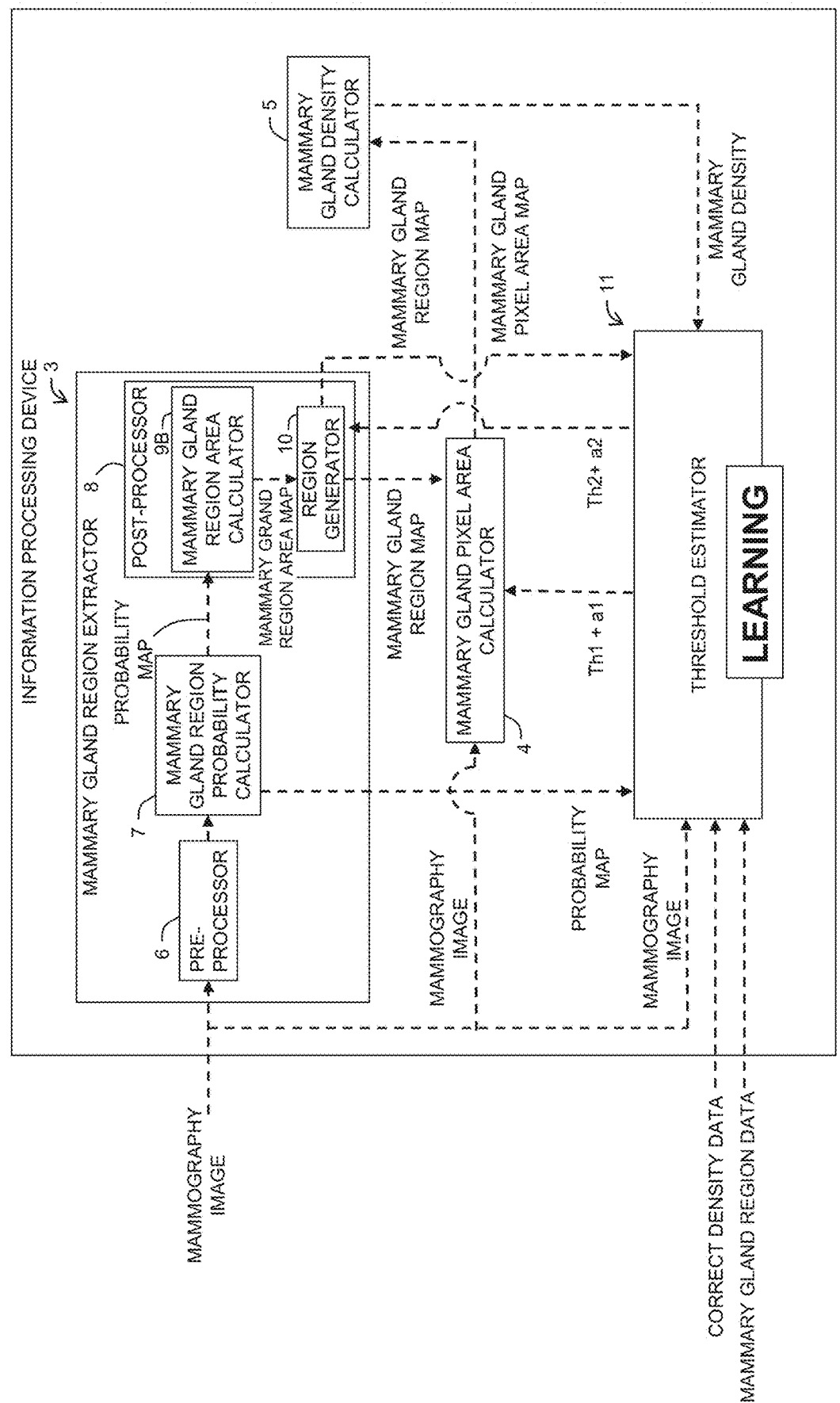

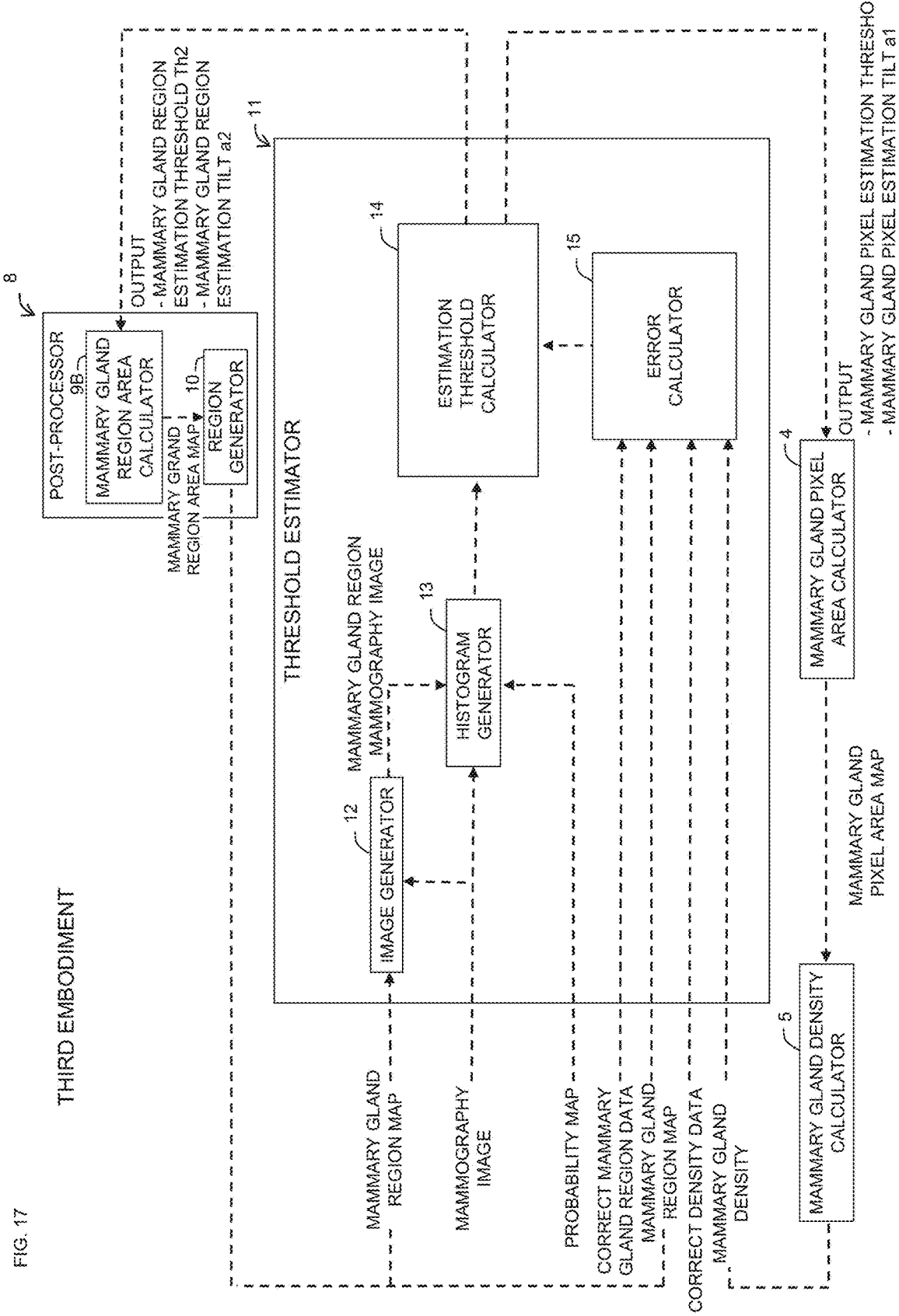

METHOD FOR LEARNING THRESHOLD VALUE

TECHNICAL FIELD

The present invention relates to a method for learning a threshold value applied to pixels in a mammography image.

BACKGROUND ART

Breast cancer screening basically uses mammography to determine calcification, tumors, and so on. However, when the density of the mammary gland in the breast is high, it may not be possible to accurately determine calcification, and so on (mostly in Japanese and young people). In these cases, more accurate screenings are performed by parallelly performing ultrasonography, which increases the screening cost and is not easily affected by the mammary gland. Thus, the interpretation doctors guide the examinees, when they judge that the mammary gland densities of the examinees are high based on the mammography images, to perform the ultrasonography diagnosis. At this time, there is no clear criterion for "the mammary gland density is high", and the criteria of the interpretation doctors are different, which is a problem.

For example, a method for calculating mammary gland density based on mammary gland ratio has been proposed (e.g., patent literature 1). In patent literature 1, the mammary gland ratio is calculated by dividing the area of the mammary gland region by the area of the breast region. The mammary region is a region consisting of pixels in the breast region whose pixel values are above a threshold. Thus, the mammary gland density can be calculated, for example, by performing a threshold process on the pixels in the mammography image.

CITATION LIST

Patent Literature

[Patent Literature 1] Japanese Unexamined Patent Application No. 2016-158963

Non-Patent Literature

[Nonpatent Literature 1] Fully Convolutional Networks for Semantic Segmentation, IEEE Transactions on Pattern Analysis and Machine Intelligence (Volume: 39, Issue: 4, Apr. 1, 2017)

SUMMARY OF INVENTION

Technical Problem

For example, from the viewpoint of improving the accuracy of calculation of mammary gland density and various values calculated in the process of calculating mammary gland density, it is preferable that the threshold used in the threshold process, for example, in patent literature 1, be acquired in a more objective method.

The present invention has been made in view of the foregoing, and an object thereof is to provide a method for learning a threshold that can provide a more objective threshold to be applied to pixels in the mammography image.

Solution to Problem

The present invention provides a method for learning a threshold value applied to pixels in a mammography image comprising: an acquiring step; and a learning step, wherein in the acquiring step, the mammography image is acquired, in the learning step, a relationship between the mammography image and a mammary gland pixel estimation threshold is learned, the mammary gland pixel estimation threshold is a threshold value used to calculate a mammary gland pixel area of each pixel of a mammary gland region in the mammography image, and the mammary gland pixel area is a value indicating a degree of a mammary gland pixel-likeness of the pixel in the mammography image.

The present invention can provide more objective mammary gland pixel estimation thresholds because the relationship between mammography images and mammary gland pixel estimation thresholds is learned in the learning step.

Various embodiments of the present invention are described below. Any of the embodiments described below can be combined with one another.

Preferably, the method further comprises a mammary gland density acquiring step, wherein in the acquiring step, a correct mammary gland density in the mammary gland region is further acquired, in the mammary gland density acquiring step, a calculated mammary gland density in the mammary gland region is acquired based on the mammography image and the mammary gland pixel estimation threshold, in the learning step, the relationship is learned based on the correct mammary gland density, and the calculated mammary gland density or the mammary gland pixel estimation threshold output in the learning step.

Preferably, in the learning step, a relationship between the mammography image and a mammary gland pixel estimation tilt is further learned, the mammary gland pixel estimation threshold is a threshold of a predetermined threshold function, the mammary gland pixel estimation tilt is a tilt of the threshold function at the mammary gland pixel estimation threshold, the threshold function is a function that associates a pixel value of each pixel in the mammary gland region with the mammary gland pixel area of each such pixel, and in the mammary gland density acquiring step, the mammary gland pixel area of each pixel in the mammary gland region is calculated based on the threshold function, the mammary gland pixel estimation threshold, and the mammary gland pixel estimation tilt, and the calculated mammary gland density is acquired based on the sum of the mammary gland pixel area.

Preferably, the method further comprises a histogram generation step, wherein in the histogram generation step, first to third histograms are generated, the first histogram is a histogram of a pixel value of each pixel in the mammography image, the second histogram is a histogram of a pixel value of each pixel in the mammary gland region, and the third histogram is a histogram of a mammary gland region probability of each pixel in the mammography image, the mammary gland region probability indicates a probability that each pixel in the mammography image is in the mammary gland region, and in the learning step, the relationship between the first to third histograms and the mammary gland pixel estimation threshold is learned.

Preferably, the mammary gland region is a narrower region than an entire breast in the mammography image.

According to another aspect of the embodiments provides a method for learning a threshold value applied to pixels in a mammography image comprising: an acquiring step; and a learning step, wherein in the acquiring step, the mammography image is acquired, in the learning step, a relationship between the mammography image and a mammary gland region estimation threshold is learned, the mammary gland region estimation threshold is a threshold value used to calculate a mammary gland region area of each pixel of a mammary gland region in the mammography image, and the mammary gland region area is a value indicating a degree to which the pixel in the mammography image constitutes the mammary gland region or not.

BRIEF DESCRIPTION OF DRAWINGS

FIG. 7A shows the pixel value Pv of each pixel in the mammary gland region map shown in FIG. 6B. FIG. 7B is a schematic diagram showing the mammary gland pixel area La of each pixel in the mammary gland region map shown in FIG. 7A.

FIG. 13 a block diagram showing a configuration of a threshold estimator 11 and configuration of a post-processor 8 according to the second embodiment.

FIG. 16 is a block diagram showing a configuration of an information processing device 1 according to the third embodiment and a flow of various data in the learning phase.

FIG. 17 is a block diagram showing a configuration of a threshold estimator 11 and a configuration of a post-processor 8 according to the third embodiment.

DESCRIPTION OF EMBODIMENTS

Embodiments of the present invention will be described below. Any of features in the embodiments described below can be combined with one another. And the invention is established independently for each feature.

1. First Embodiment

Figure 1:
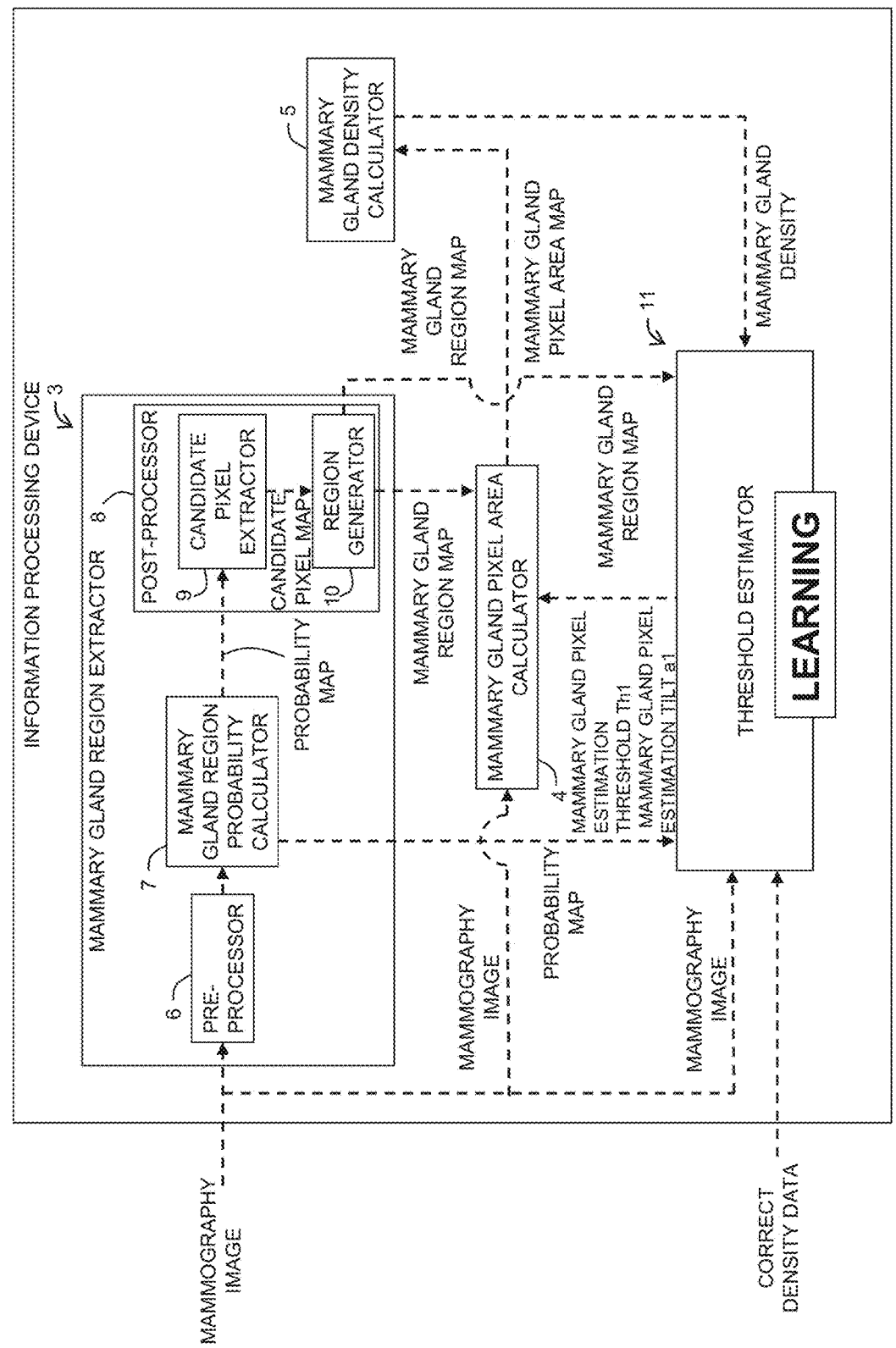
FIG. 1 is a block diagram showing a configuration of an information processing device 1 according to the first embodiment of the present invention and a flow of various data in the learning phase.

As shown in FIG. 1, an information processing device 1 according to the first embodiment includes a mammary gland region extractor 3, a mammary gland pixel area calculator 4, a mammary gland density calculator 5, and a threshold estimator 11.

Each of the above components may be realized by software or hardware. When realized by software, various functions can be realized by the CPU executing computer programs. The program may be stored in built-in memory or a non-transitory readable medium by a computer. Alternatively, the above functions are realized by reading the program stored in external memory using so-called cloud computing. When realized by hardware, the above functions can be performed by various circuits such as ASIC, FPGA, or DRP. The first embodiment deals with various information and concepts including this information, and the various information is a bit group of binary numbers having 0 or 1, and the various information is represented according to the level of signal value. And in the present embodiment, communications and calculations can be executed according to configurations of the above software and hardware.

1-1. Configuration Description 1-1-1. Mammary Gland Region Extractor 3

Figure 4A:
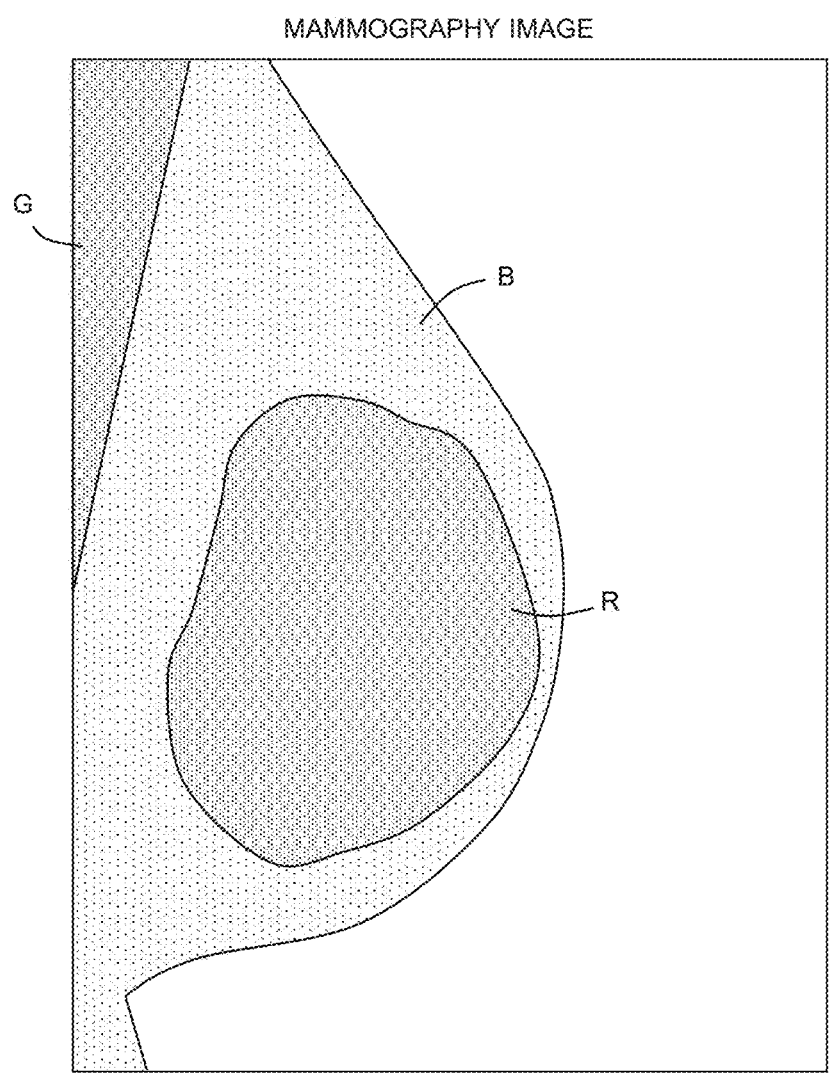
FIG. 4A is a schematic diagram of the mammography image.

The mammary gland region extractor 3 is configured to extract a mammary gland region R in a mammography image as shown in FIG. 4A. The mammography image is a digital image having a large number of pixels. Each pixel has a brightness value. The mammography image usually includes the pectoralis major muscle region G and the breast region B. The pectoralis major muscle region G is the region corresponding to the pectoralis major muscle, and the breast region B is the region corresponding to the entire breast. Breast region B includes the mammary gland region R. The mammary gland region R is a narrower region than the mammary gland region R. The mammary gland region R includes mammary gland pixels and fat pixels. The mammary gland pixels are pixels corresponding to the mammary gland. The fat pixels are pixels corresponding to the fat, and are pixels other than the mammary gland pixels in the mammary gland region R. The mammary gland region R is the region that roughly encloses the mammary gland pixel.

In FIG. 4A, for convenience of illustration, the mammary gland region R is surrounded by a solid line. But the actual mammography image has no solid line surrounding the mammary gland region R, and a part corresponding to the mammary gland is displayed in high brightness. Since the boundary of the part corresponding to the mammary gland is unclearly distributed like a cloud and it is difficult to uniquely define the boundary. Thus, the first embodiment extracts the mammary gland region R based on the probability P that a region in the mammography image is the mammary gland region R. The solid lines showing the pectoralis major muscle region G and breast region B do not exist in the actual mammography image.

As shown in FIG. 1, the mammary gland region extractor 3 includes a pre-processor 6, a mammary gland region probability calculator 7, and a post-processor 8. Hereinafter, each configuration will be described in detail.

<Pre-Processor 6>

The pre-processor 6 is configured to perform various preprocessing on the mammography image. The preprocessing is performed to bring the mammography image into an image suitable for processing in the mammary gland region probability calculator 7. The preprocessed image is also called the mammography image.

The pre-processor 6 includes a size adjustment part, a window level adjustment part, and a noise removing part. Part or all of the pre-processor 6 may be omitted if not needed.

Size Adjustment Part

The size adjustment part is configured to adjust the size of the mammography image. The resolution of the mammography image varies depending on the imaging equipment and settings. This means that the actual size (mm) per pixel differs depending on an input image. The size adjustment part resizes the mammography image to, for example, 0.2 mm per pixel to eliminate fluctuations in detection accuracy due to a size difference per pixel. For example, if the pre-processor 6 has a limited amount of computation or processing speed, the size adjustment part can also resize each image to a predetermined uniform image size.

Window Level Adjustment Part

The window level adjustment part is configured to adjust the window level of the mammography image. Window level adjustment is a process for improving the contrast in a specific gradation range of an image having a wide range of gradation values. The visibility of the mammography image can be improved by adjusting the window level. As a result, the extraction accuracy of the mammary gland region R can be improved.

Noise Removing Part

The noise removing part is configured to remove noise from the mammography image. Some mammography images may include the pixels that reduce the extraction accuracy of the mammary gland region R. The noise removing part removes them as noise. Examples of noise include artificial labels and pectoralis major muscle region G. The artificial label is artificially attached and can be removed by masking. The pectoralis major muscle region G can be removed by known region expansion methods. However, in the first embodiment, since the mammary gland region R can be extracted even when the mammography image includes the pectoralis major muscle region G, the pectoralis major muscle region G does not have to be treated as noise.

The order of the size adjustment, the window level adjustment, and the noise removal may be appropriately changed.

<Mammary Gland Region Probability Calculator 7>

The mammary gland region probability calculator 7 calculates probability P, the mammary gland region R, for each of the segmented regions in the mammography image. Specifically, the mammary gland region probability calculator 7 generates a probability map in which the probability P that is the mammary gland region R is identified for each of the regions concerned. In the first embodiment, the probability map spans the entire area of the mammography image. In the first embodiment, the size adjustment part resizes the mammography image (reduces in the first embodiment), and this resized mammography image is input to the mammary gland region probability calculator 7 so that the, Each of the segmented regions in the mammography image described above is rougher than each pixel in the mammography image. In other words, the range of each of these regions is wider than each pixel in the mammography image. Thus, in the first embodiment, the mammography image processed by the mammary gland region probability calculator 7 may be a reduced image of the mammography image acquired by mammography measurement.

Commonly, in the mammography images, the brightness values of the pectoralis major muscle region G and the mammary gland region R (especially the mammary gland pixel) are higher than that of other regions (in other words, X-ray transmittance is lower than that of other regions). The brightness values of the pectoralis major muscle region G and the mammary gland region R are similar, and it is difficult to distinguish between the pectoralis major muscle region G and the mammary gland region R by brightness values. Thus, the information processing device 1 of the first embodiment calculates the probability P indicating whether each pixel in the mammography image is the mammary gland region R, and extracts the mammary gland region R based on the probability P. Since the probability P is low in the pectoralis major muscle region G and is high in the mammary gland region R, it is possible to improve the detection accuracy of the mammary gland region R by extracting the mammary gland region R based on the probability P. Besides, the probability P can be calculated without removing the pectoralis major muscle region in the mammography image. The probability P is expressed by a value in the range of 0 to 1, for example. And the higher this value, the higher the probability P that the corresponding pixel is the mammary gland region.

The probability P can be calculated based on the learning model that outputs the probability P when the mammography image is input. In the first embodiment, an FCN (Fully Convolutional Network), a type of convolutional neural network, can be employed as the learning model (machine learning model) for the mammary gland region probability calculator 7. The details of the FCN are disclosed in the non-patent literature 1. Note that the learning of the mammary gland region probability calculator 7 has been completed in the first implementation. Here, the threshold estimator 11 shown in FIG. 1 is in the learning phase, whereas the learning of the mammary gland region probability calculator 7 shown in FIG. 1 has already been completed. In other words, the weight coefficients of the filters in the neural network of threshold estimator 11 are not fixed and are updated as needed, while the weight coefficients of the filters in the neural network of the mammary gland region probability calculator 7 are already fixed.

<Post-Processor 8>

The post-processor 8 is configured to extract the mammary gland region R based on the probability P. The post-processor 8 includes a candidate pixel extractor 9 and a region generator 10.

Candidate Pixel Extractor 9

The candidate pixel extractor 9 is configured to generate a candidate pixel map by extracting pixels, whose probability P exceeds a mammary gland region estimation threshold Th2, as candidate pixels, and is configured to output the candidate pixel map. In the first embodiment, the mammary gland region estimation threshold Th2 is a predetermined value. The mammary gland region estimation threshold Th2 may be a fixed value or a value that can be changed by the users as appropriate. The candidate pixel map has pixels corresponding to the pixels of the probability map. In the candidate pixel map, the value of the pixel whose the probability P is greater than or equal to the mammary gland region estimation threshold Th2 is, for example, 1, and the value of the pixel whose the probability P is less than the mammary gland region estimation threshold Th2 is, for example, 0.

Figure 5A:
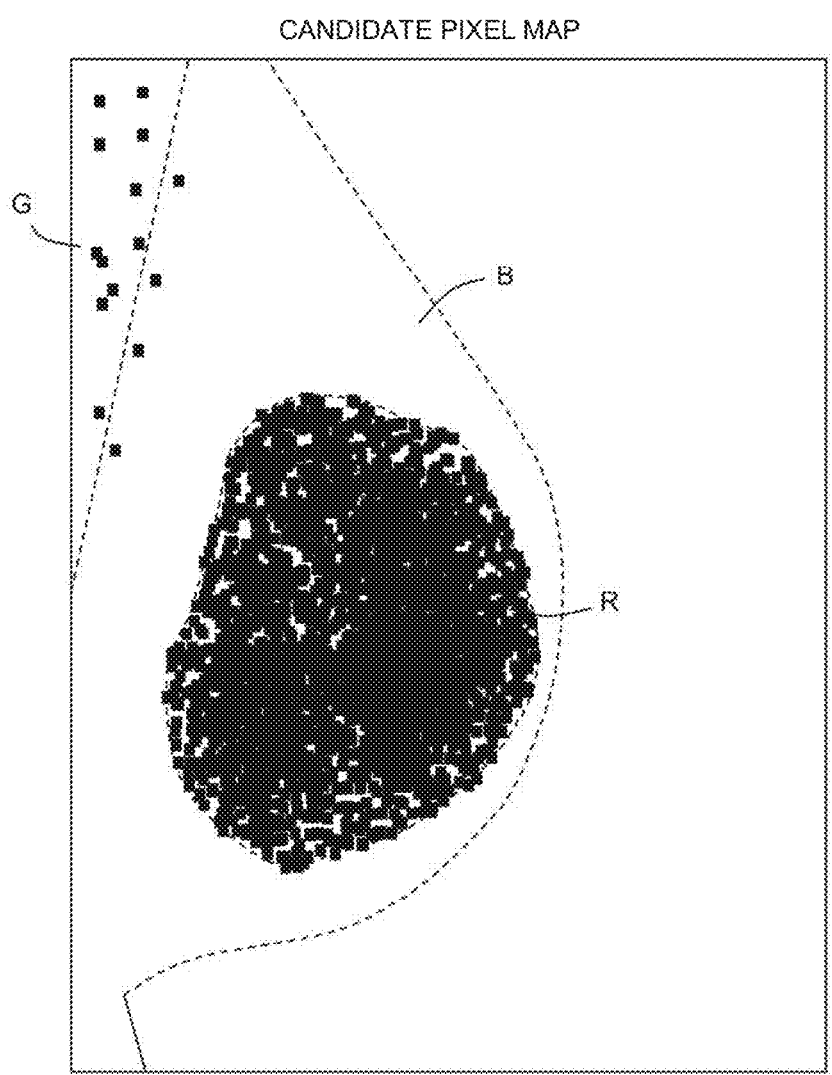
FIG. 5A is a schematic diagram of an example of a candidate pixel map.

An example of the candidate pixel map is shown in FIG. 5A. The candidate pixels are indicated by black dots. The boundaries of the pectoralis major muscle region G, the mammary gland region R, and the mammary gland region R are shown by dotted lines for reference. Regarding the candidate pixel map, a large number of the candidate pixels are extracted in the region corresponding to the mammary gland region R, and a small number of the candidate pixels are also extracted in the region corresponding to the pectoralis major muscle region G. A large number of the candidate pixels are concentrated in the region corresponding to the mammary gland region R, but there are missing regions (a white region in the mammary gland regions R of FIG. 5A) between the candidate pixels. Therefore, this mammary gland region R does not form one region.

Region Generator 10

The region generator 10 is configured to form the mammary gland region R by removing noise and filling in the missing regions with respect to the candidate pixel map.

Figure 5B:
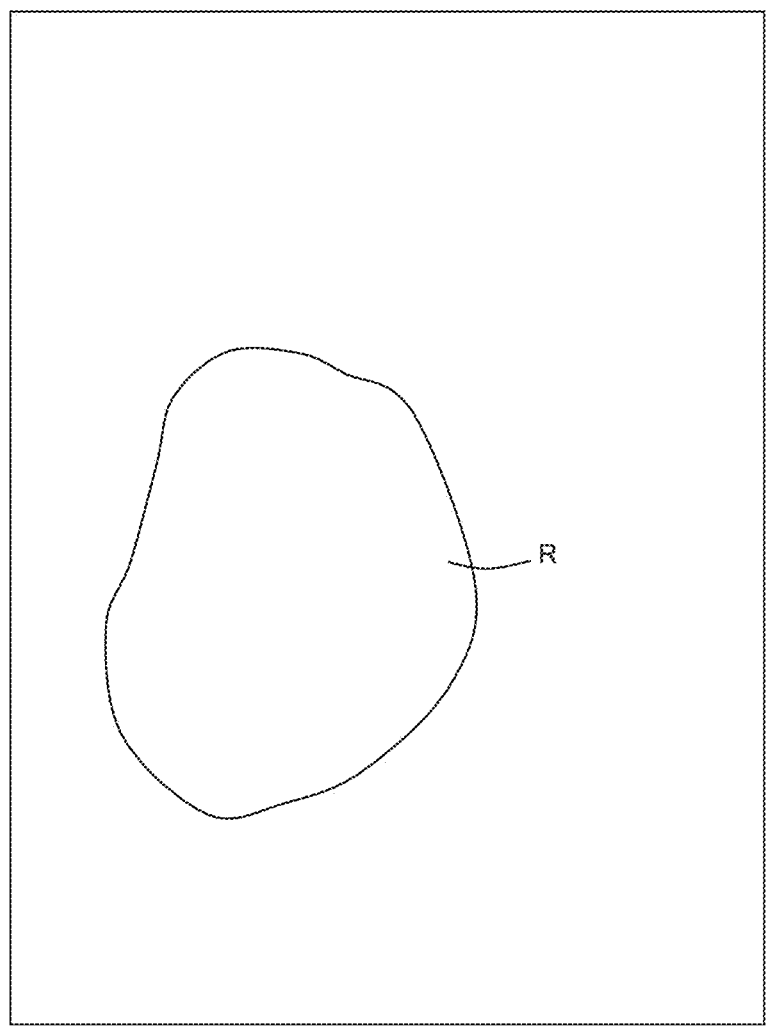
FIG. 5B is a schematic diagram of an example mammary gland region map.

Specifically, the candidate pixel in the region corresponding to the pectoralis major muscle region G is regarded as noise and is removed by processing such as mask processing. Besides, for the region corresponding to the mammary gland region R, the missing regions are filled to form the mammary gland region R. The missing region may be filled in, for example, by filling in space from the start point to the end point of each of the columns and rows. This gives the mammary gland region map as shown in FIG. 5B. Since the mammary gland region R is formed in the region where the candidate pixels are concentrated, it is preferable to ignore the candidate pixels, far from the region where the candidate pixels are concentrated, as noise in the missing region filling step. For example, even when the start points of the column or the row is detected, the detected start point may be discarded and a new start point may be searched when a predetermined number or more of non-candidate pixels are consecutive after the start point is detected.

When the pectoralis major muscle region G is removed from the mammography image in advance, the noise removal step may be omitted. Furthermore, in the processing of filling in the missing region, the candidate pixels in the pectoralis major muscle region G and the candidate pixels that exist outside the pectoralis major muscle region G and outside the region where the candidate pixels are concentrated can be removed by ignoring the candidate pixels that are far from the region where the candidate pixels are concentrated. Therefore, it is possible to form the mammary gland region R in the missing region filling step without performing the noise removal step.

1-1-2. Mammary Gland Pixel Area Calculator 4

The mammary gland pixel area calculator 4 generates a mammary gland pixel area map as shown in FIG. 7B. The mammary gland pixel area map is a map in which the mammary gland pixel area La is calculated for each pixel in the mammary gland region R. The mammary gland pixel area La is a value that indicates a degree of the mammary gland pixel-likeness of the pixels.

Figure 6A:
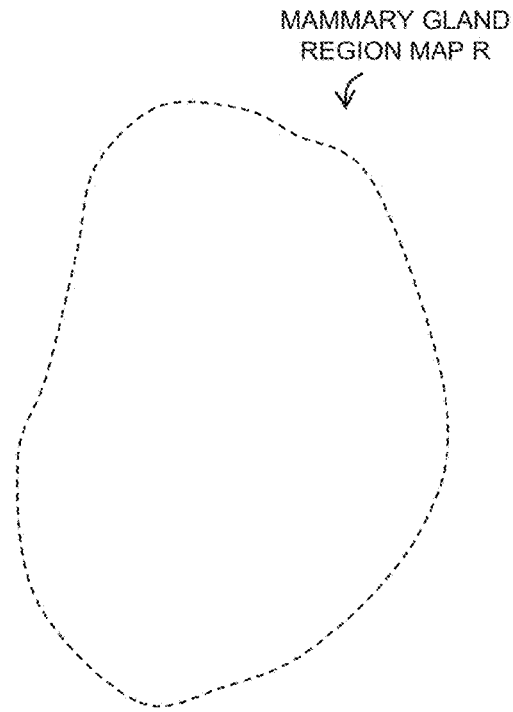
FIG. 6A is a schematic diagram of the example mammary gland region map.
Figure 6B:
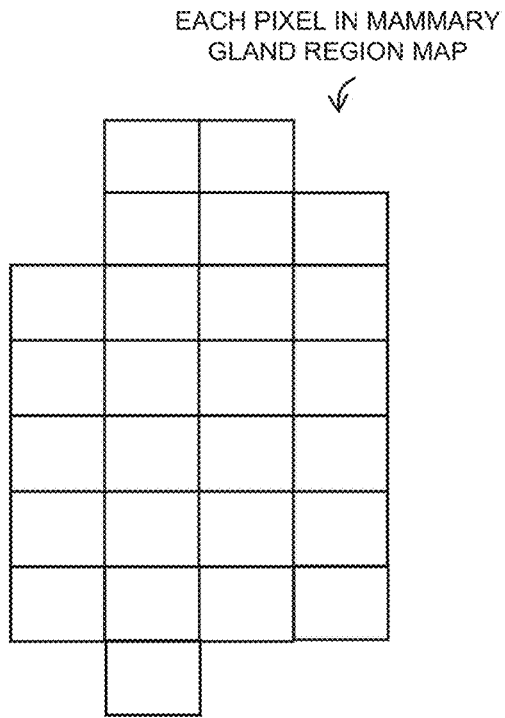
FIG. 6B is a schematic diagram showing each pixel included in the mammary gland region map shown in FIG. 6A.

The mammary gland pixel area calculator 4 applies the mammary gland region map acquired from the region generator 10 of the post-processor 8 to the mammography image. As the result, the mammary gland pixel area calculator 4 extracts the pixels in the mammary gland region R from the pixels in the mammography image. The mammary gland region R is shown schematically in FIG. 6A, and the pixels in the mammary gland region R are shown schematically in FIG. 6B.

The mammary gland pixel area calculator 4 performs the first pixel area calculation process for the extracted pixel (the pixel in the mammary gland region R). The first pixel area calculation process calculates the mammary gland pixel area La based on the pixel values Pv of the pixels in mammary gland region R of the mammography image. The pixel value Pv of each extracted pixel is schematically shown in FIG. 7A. Also, FIG. 7B schematically shows the pixels in the mammary gland region R where the mammary gland pixel area La was calculated (the first pixel area calculation process was performed). Next, the mammary gland pixel area calculator 4 uses the first threshold function to calculate the mammary gland pixel area La. Next, the first threshold function, the mammary gland pixel area La, etc. will be further described.

First Threshold Function

Figure 8:
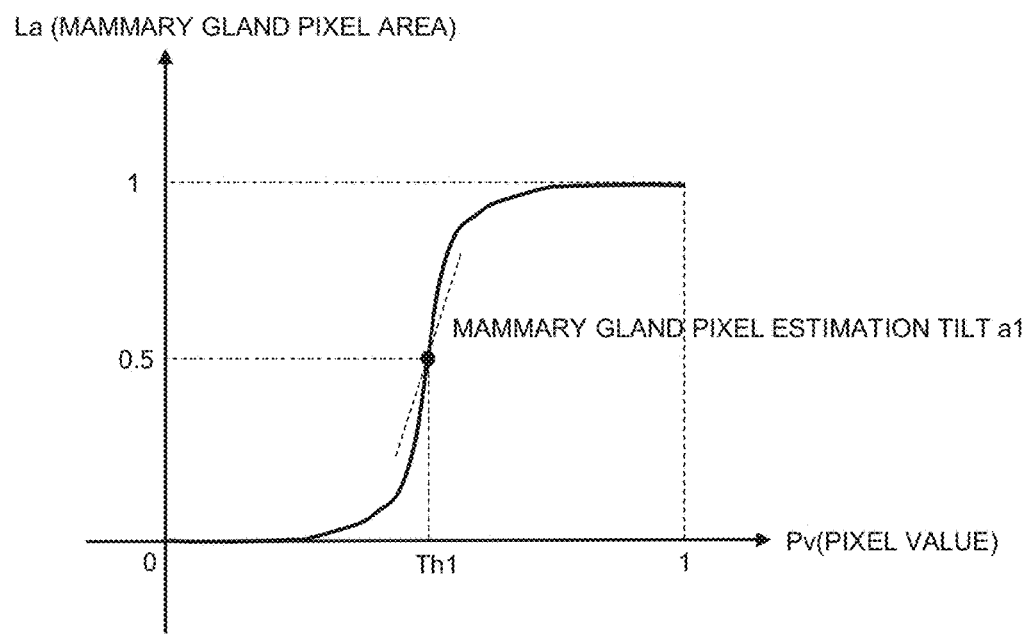
FIG. 8 is an illustration of the first threshold function (sigmoid function) that defines the relationship between the probability P and the mammary gland pixel area La of each pixel in the mammary gland region map.

When the mammary gland pixel area calculator 4 calculates the mammary gland pixel area La based on the pixel values Pv of the pixels in the mammography image, the mammary gland pixel area calculator 4 uses the first threshold function shown in FIG. 8. The first threshold function is a function that associates the pixel value Pv of each pixel in the mammary gland region R with the mammary gland pixel area of each pixel in the mammary gland region R. Also, the first threshold function is a function that rises sharply at the mammary gland pixel estimation threshold Th1. That is, in the first threshold function, in the range of pixel values Pv less than the mammary gland pixel estimation threshold Th1, the value of mammary gland pixel area La is 0 or close to 0, in the range of pixel values Pv greater than the mammary gland pixel estimation threshold Th1, the value of mammary gland pixel area La is 1 or close to 1. Thus, the mammary gland pixel estimation threshold Th1 is the threshold in the first threshold function. The first threshold function (sigmoid function) of the first embodiment is represented by the formula shown in FIG. 8, the curve shape of the first threshold function (sigmoid function) of the first embodiment is determined by determining the mammary gland pixel estimation threshold Th1 and mammary gland pixel estimation tilt a1. The mammary gland pixel estimation tilt a1 corresponds to the tilt of the first threshold function when the pixel values Pv of the first threshold function is the mammary gland pixel estimation threshold Th1.

In the first embodiment, the first threshold function is a sigmoid function, but other functions can also be employed. For example, a continuous function whose function value goes from 0 to 1 can be employed for the first threshold function. Specifically, $f(x)=(\tan h(x)+1)/2$ can be employed for the first threshold function.

Output: Mammary Gland Pixel Area La

The mammary gland pixel area La is a value that indicates a degree of mammary gland pixel-likeness, as described above. For example, if the mammary gland pixel area La of a given pixel is 1, the given pixel can be regarded as a mammary gland pixel itself, and if the mammary gland pixel area La of a given pixel is 0, the given pixel cannot be regarded as a mammary gland pixel. In addition, the mammary gland pixel area La can be an intermediate value that is greater than 0 and less than 1.

That is, the mammary gland pixel area calculator 4 does not determine whether a pixel in the mammography image is a mammary gland pixel or a non-mammary gland pixel. In other words, the mammary gland pixel area La is not a value that can be used to clearly distinguish whether a given pixel is a mammary gland pixel or not.

In an embodiment, the mammary gland pixel area La is not calculated for any given pixel, but for pixels in the mammary gland region R. That is, the mammary gland pixel area calculator 4 calculates the mammary gland pixel area La in the mammary gland region R based on the pixel value Pv of the pixel in the mammary gland region R within the mammography image.

Although it is also possible for the mammary gland pixel area calculator 4 to generate a mammary gland pixel area map in which the mammary gland pixel area La is calculated for each region of the probability map, in the first embodiment, the mammary gland pixel area calculator 4 generates a mammary gland pixel area map in which the mammary gland pixel area La is calculated for each pixel in the mammography image. And each pixel in the mammography image is finer than each region in the probability map. Therefore, the mammary gland pixel area calculator 4 can generate a more fine-grained mammary gland pixel area map.

Input: Mammary Gland Pixel Estimation Threshold Th1 and Mammary Gland Pixel Estimation Tilt a1 mammary gland pixel area calculator 4 receives the mammary gland pixel estimation threshold Th1 and the mammary gland pixel estimation tilt a1 from a threshold estimator 11. Then, the mammary gland pixel area calculator 4 calculates the mammary gland pixel area La of the pixel in the mammary gland region R based on the pixel value Pv of the pixel in the mammary gland region R and the first threshold function to which the mammary gland pixel estimation threshold Th1 and the mammary gland pixel estimation tilt a1 are assigned. In the first embodiment, the case where the mammary gland pixel estimation tilt a1 is calculated by the threshold estimator 11 and the calculated mammary gland pixel estimation tilt a1 is received by the mammary gland pixel area calculator 4 will be described as an example, but the present invention is limited to this. For example, the mammary gland pixel estimation tilt a1 may be a fixed value or a value that can be changed by the users as appropriate.

1-1-3. Mammary Gland Density Calculator 5

The mammary gland density calculator 5 calculates the mammary gland density based on the sum of the mammary gland pixel area La of all pixels in the mammary gland region R. More specifically, the mammary gland density calculator 5 calculates the sum of the mammary gland pixel area La of all pixels in the mammary gland region R and the number of all pixels in the mammary gland region R, the mammary gland density calculator 5 calculates the mammary gland density based on the following formula.

The mammary gland density (%)=100×(the sum of mammary gland pixel area La)/(the total number of the pixels in mammary gland region)

The mammary gland density calculated by the mammary gland density calculator 5 corresponds to the calculated mammary gland density.

In the learning phase, the mammary gland density calculated by the mammary gland density calculator 5 is output from the mammary gland density calculator 5 to the threshold estimator 11 and is used to adjust the filter weight coefficients of the neural network of the threshold estimator 11. In the operational phase, the mammary gland density calculated by the mammary gland density calculator 5 is used as information to appropriately determine whether an ultrasound examination is necessary or not. The mammary gland density calculated in this manner will be high if there is a high density of the mammary gland region in a narrow region. Therefore, even when there is a high density of the mammary gland region in a narrow region, the information processing device 1 according to the first embodiment can provide information that can appropriately determine whether an ultrasound examination is necessary or not. The calculated mammary gland density can be used to display it on the display of the information processing device 1 or output it from the information processing device 1 to an external device.

1-1-4. Threshold Estimator 11

Figure 3:
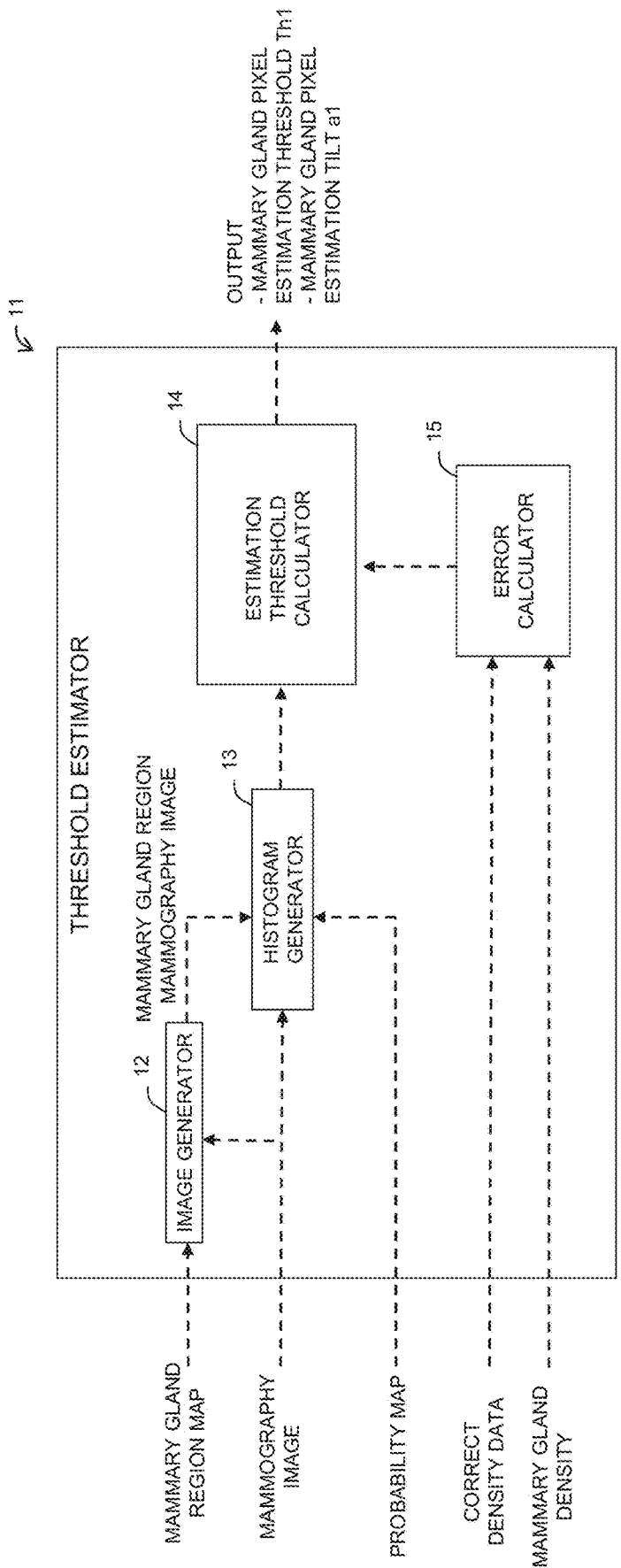
FIG. 3 is a block diagram showing a configuration of a threshold estimator 11.

The threshold estimator 11 has the function of calculating the mammary gland pixel estimation threshold Th1 and the mammary gland pixel estimation tilt a1 (see FIG. 8) based on the mammography images in the learning phase and the operational phase. The threshold estimator 11 includes an image generator 12, a histogram generator 13, an estimation threshold calculator 14, and an error calculator 15, as shown in FIG. 3.

<Image Generator 12>

Figure 4B:
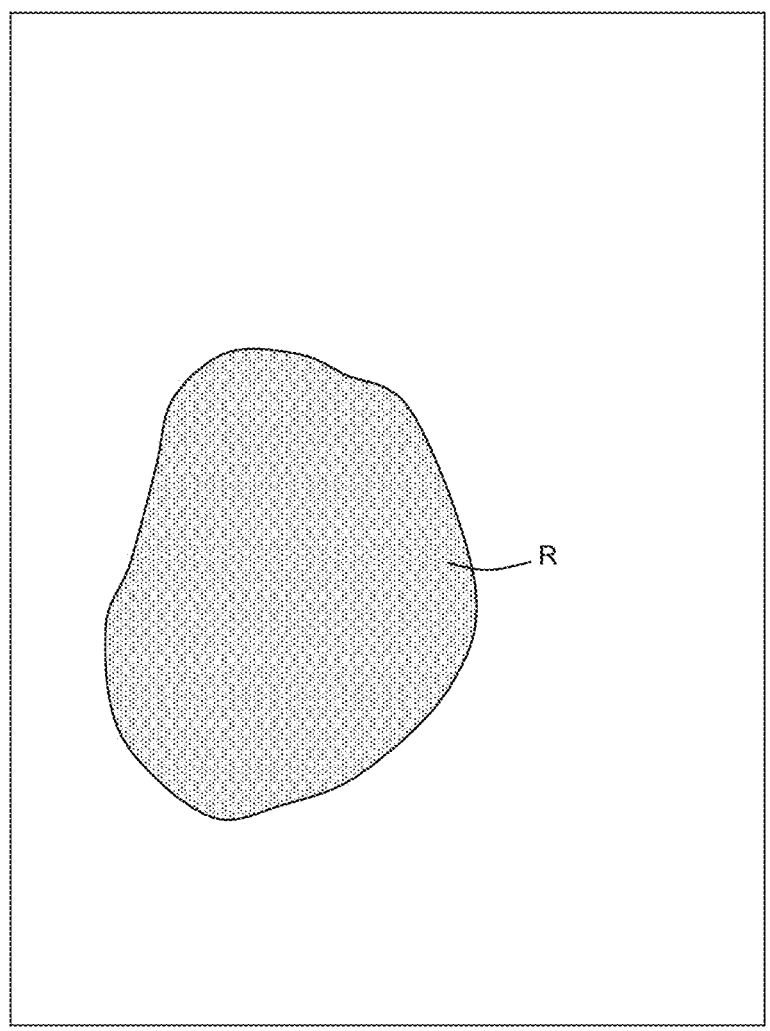
FIG. 4B is a schematic diagram showing an example of a mammary gland region mammography image.

The image generator 12 generates the mammary gland region mammography image based on the mammography image. The mammary gland region mammography image shown in FIG. 4B is comprised of the pixels in the mammary gland region R within the mammography image. The image generator 12 can generate the mammary gland region mammography image based on the mammary gland region map and the mammography image.

<Histogram Generator 13>

The histogram generator 13 generates the first through third histograms. Specifically, the histogram generator 13 generates the first histogram based on the mammography image, the second histogram based on the mammary gland region mammography image generated by the image generator 12, and the third histogram based on the probability map generated by the mammary gland region probability calculator 7.

The first histogram is a histogram of the pixel values of each pixel in the mammography image. In the first histogram, a plurality of the pixel values or the ranges of the pixel values are predetermined, and the number of pixels that belongs to the predetermined pixel values or the ranges of the pixel values is specified.

The second histogram is a histogram of the pixel values of each pixel in the mammary gland region mammography image generated by the image generator 12. In the second histogram, a plurality of the pixel values or the ranges of the pixel values are predetermined, and the number of the pixels that belongs to the predetermined pixel values or the ranges of the pixel values is specified.

The third histogram is a histogram of the probability P of each pixel in the mammography image. In the third histogram, a plurality of the probability P or the ranges of the probability P are predetermined, and the number of the pixels that belongs to the predetermined probability P or the ranges of probability P is specified.

<Estimation Threshold Calculator 14>

In the learning phase, the estimation threshold calculator 14 has the function of learning the relationship between the mammography image and the values related to the first threshold function (the mammary gland pixel estimation threshold Th1 and the mammary gland pixel estimation tilt a1). In the first embodiment, the estimation threshold calculator 14 uses the probability map generated from the mammography image and the mammary gland region mammography image generated from the mammography image, in addition to the mammography image during learning.

The estimation threshold calculator 14 has a neural network, and when the mammography image is input, the estimation threshold calculator 14 learns based on a learning model that outputs the mammary gland pixel estimation threshold Th1 and the mammary gland pixel estimation tilt a1. Also, the filter weight coefficients of the neural network of the estimation threshold calculator 14 are updated appropriately based on the error calculated by the error calculator 15. Specifically, as shown in FIG. 1, when the estimation threshold calculator 14 outputs the mammary gland pixel estimation threshold Th1 and the mammary gland pixel estimation tilt a1, then, the mammary gland pixel area calculator 4 calculates the mammary gland pixel area La of each pixel in the mammary gland region R based on the first threshold function to generate the mammary gland pixel area map. Then, the mammary gland density calculator 5 calculates the mammary gland density based on the mammary gland pixel area map. This calculated mammary gland density is output to the threshold estimator 11 and compared with the correct density data described below. Then, the estimation threshold calculator 14 receives the difference (error) between the mammary gland density calculated by the mammary gland density calculator 5 and the correct density data from the error calculator 15. This allows the filter weight coefficients of the neural network in the estimation threshold calculator 14 to be updated appropriately based on this error.

In the first embodiment, the image data is not input to the estimation threshold calculator 14, but the first to third histograms are input. Therefore, the neural network of the estimation threshold calculator 14 has a reduced computing load.

<Error Calculator 15>

The error calculator 15, as shown in FIGS. 1 and 3, compares the correct mammary gland density data (the correct mammary gland density) input to the information processing device 1 with the mammary gland density calculated by the mammary gland density calculator 5. That is, the error calculator 15 calculates the difference (error) between the correct density and the calculated mammary gland density. Here, the correct density data is the correct data in which the mammary gland density has been determined by a doctor or other person. In other words, the correct density data is the value of the mammary gland density calculated by a doctor or other person who visually examines the corresponding mammography image. The error calculator 15 outputs the calculated difference (error) to the estimation threshold calculator 14.

1-2. Operation Description 1-2-1. Learning Phase

The operation in the learning phase of the mammary gland pixel estimation threshold Th1 is described with reference to FIG. 1 and FIG. 3.

The learning method of the first embodiment has an acquiring step, a probability map generating step, a mammary gland region extracting step, an image generating step, a histogram generating step, a learning step, a mammary gland pixel area map generating step, and a mammary gland density acquiring step.

In the acquiring step, the information processing device 1 acquires the mammography image. In the acquiring step, the mammography image is received by the mammary gland region extractor 3, the mammary gland pixel area calculator 4 and the threshold estimator 11. Also, in the acquiring step, the information processing device 1 acquires the correct density data. Furthermore, in the acquiring step, the error calculator 15 receives the correct density data.

In the probability map generating step, the mammary gland region probability calculator 7 generates a probability map based on the mammography image that has been pre-processed. probability calculator 7 outputs the probability map to the post-processor 8 and threshold estimator 11.

In the mammary gland region extracting step, the candidate pixel extractor 9 generates a candidate pixel map based on the probability map, and the region generator 10 generates the mammary gland region map based on the candidate pixel map. The region generator 10 outputs the mammary gland region map to the mammary gland pixel area calculator 4 and the threshold estimator 11.

In the image generating step, the image generator 12 generates the mammary gland region mammography image based on the mammography image acquired in the acquiring step.

In the histogram generating step, the histogram generator 13 generates the first through third histograms based on the mammography image. More specifically, in the histogram generating step, the histogram generator 13 generates the first through third histograms based on the mammography image acquired in the acquiring step, the mammary gland region mammography image generated in the image generating step, and the probability map generated in the probability map generating step. The histogram generator 13 outputs the first through third histograms to the estimation threshold calculator 14.

In the learning step, the estimation threshold calculator 14 learns a relationship between the mammography image and the mammary gland pixel estimation threshold Th1. More specifically, the estimation threshold calculator 14 learns the relationship between the mammography image and the mammary gland pixel estimation threshold Th1, and the relationship between the mammography image and the mammary gland pixel estimation tilt a1, because the mammary gland pixel estimation tilt a1 is also a learning target in the first embodiment.

In the first embodiment, the neural network of the estimation threshold calculator 14 is not configured to process the mammography image itself, but to process the histogram, from the viewpoint of suppressing the computing load. In other words, the estimation threshold calculator 14 learns the relationship between the first through third histograms generated in the histogram generating step and the mammary gland pixel estimation threshold Th1, etc.

In the learning step, the error calculated by the error calculator 15 is input to the estimation threshold calculator 14. This error corresponds to the difference between the mammary gland density acquired in the mammary gland density acquiring step (described below) and the correct density data. As a result, the weight coefficients of the filters of the estimation threshold calculator 14 are updated accordingly, and the accuracy of the output of the estimation threshold calculator 14 (the mammary gland pixel estimation threshold Th1 and the mammary gland pixel estimation tilt a1) will be increased. In other words, the mammary gland density calculated by the information processing device 1 is calculated based on the mammary gland pixel estimation threshold Th1, etc., the mammary gland density calculated by the information processing device 1 is compared with the correct density data as the correct data, and the weight coefficient of the filter of the estimation threshold calculator 14 is updated accordingly. From the above, in the learning step, the estimation threshold calculator 14 learns the relationship between the mammography image and the mammary gland pixel estimation threshold Th1, and can calculate a more objective mammary gland pixel estimation threshold Th1.

In the mammary gland pixel area map generating step, the mammary gland pixel area calculator 4 generates the mammary gland pixel area map based on the mammography image acquired in the acquiring step and the mammary gland pixel estimation threshold Th1 and the mammary gland pixel estimation tilt a1 calculated in the learning step.

In the mammary gland density acquiring step, the mammary gland density calculator 5 acquires the mammary gland density based on the mammary gland pixel area map. mammary gland density calculator 5 outputs the mammary gland density calculated to the error calculator 15 of the threshold estimator 11.

1-2-2. Operational Phase

Figure 2:
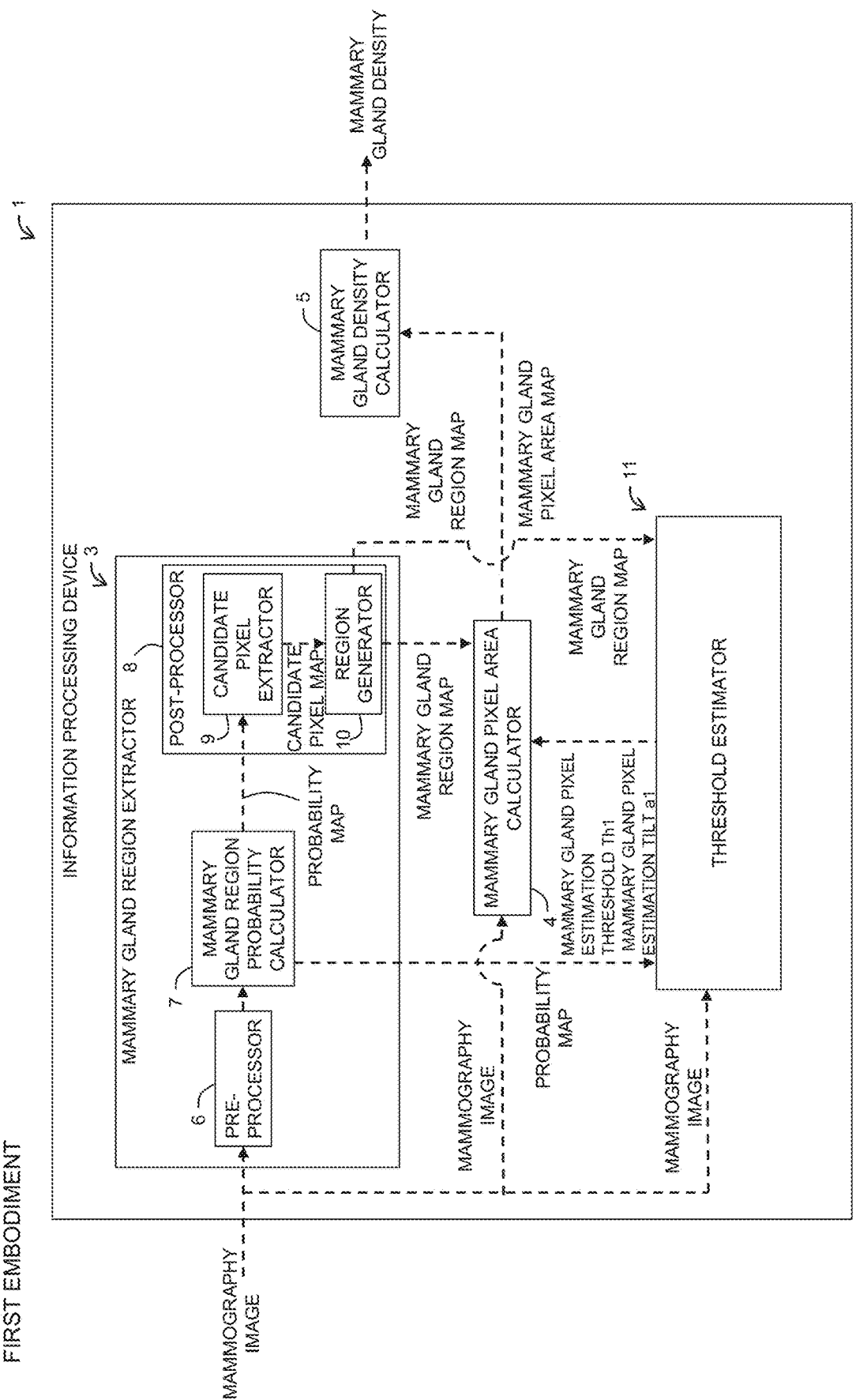
FIG. 2 is a flow of various data in the operational phase with reference to the block diagram shown in FIG. 1.

The operations in the operational phase are described based on FIG. 2. This paragraph describes only the parts of the operations in the operational phase that are different from the operations in the learning phase.

The operational method of the first embodiment (the acquisition method of the mammary gland density) includes an acquiring step, a probability map generating step, a mammary gland region extracting step, an image generating step, a histogram generating step, a threshold/tilt value calculating step, the mammary gland pixel area map generating step, and the mammary gland density acquiring step.

The probability map generating step, the mammary gland region extracting step, the image generating step, the histogram generating step, the mammary gland pixel area map generating step, and the mammary gland density acquiring step are the same as in the learning phase.

The calculation method for the mammary gland pixels in the operational phase has a threshold and tilt calculating step instead of a learning step.

In the acquiring step, the information processing device 1 does not acquire the correct density data.

In the operational phase, the weight coefficients of the filters in the estimation threshold calculator 14 are fixed. That is, the error calculator 15 does not calculate the error, so the estimation threshold calculator 14 does not acquire the error from the error calculator 15. In the learning step, the estimation threshold calculator 14 outputs the mammary gland pixel estimation threshold Th1 and the mammary gland pixel estimation tilt a1 when the first through third histograms are input.

In the operational phase, the information processing device 1 displays the mammary gland density acquired in the mammary gland density acquiring step on the display of the information processing device 1 or output it from the information processing device 1 to an external device.

Figure 9:
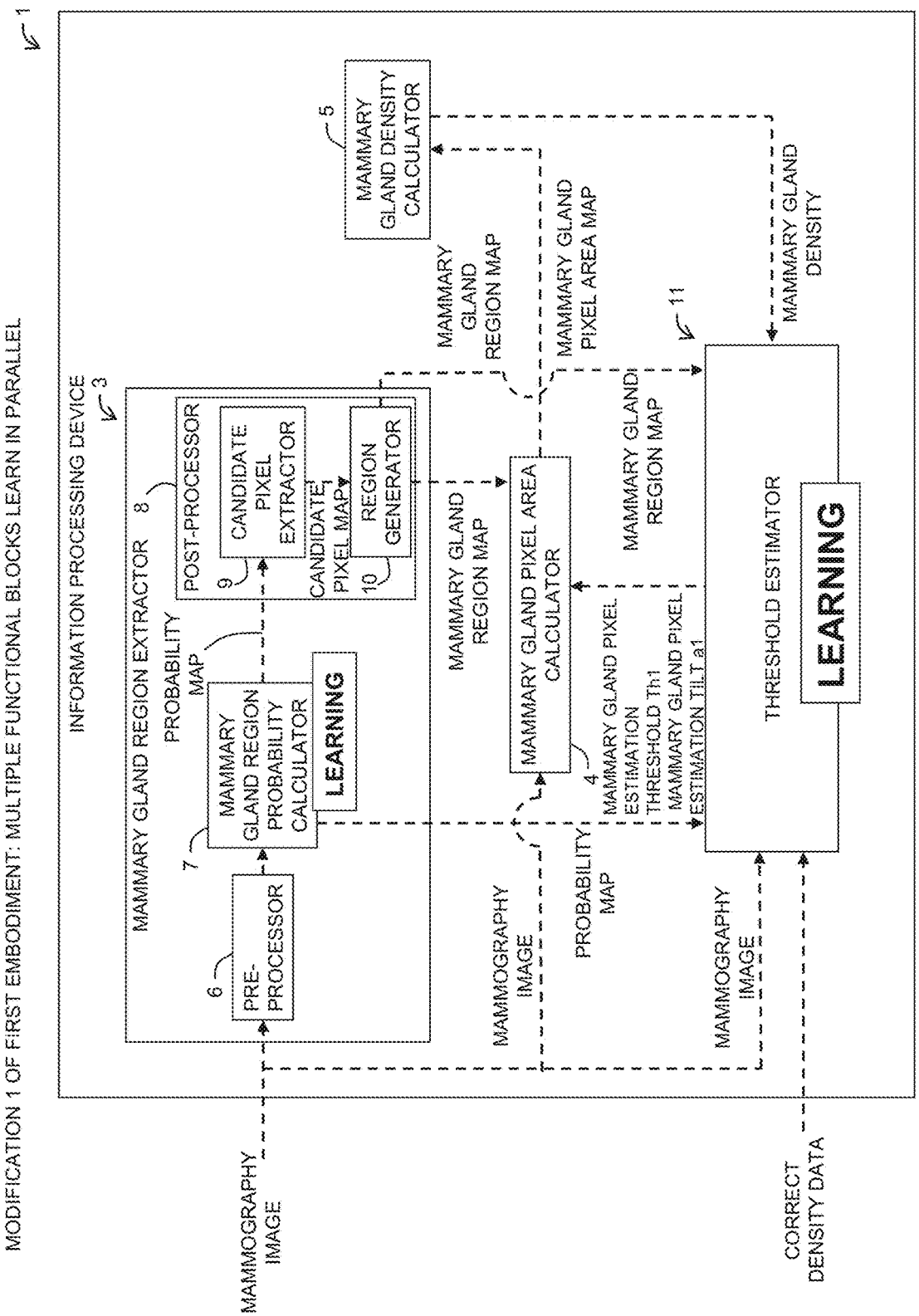
FIG. 9 is a block diagram showing a configuration of an information processing device 1 according to modification 1 of the first embodiment and a flow of various data in the learning phase.

1-3. Modifications 1-3-1. Modification 1: Multiple Functional Blocks Learn in Parallel In the embodiment, the case where the mammary gland region probability calculator 7 has completed the learning in the learning stage of the threshold estimator 11 has been described as an example, but the present invention is not limited to this. As shown in FIG. 9, information processing device 1 may be configured so that the threshold estimator 11 and the mammary gland region probability calculator 7 learn in parallel.

1-3-2. Modification 2: do not Use Histogram as Input

Figure 10:
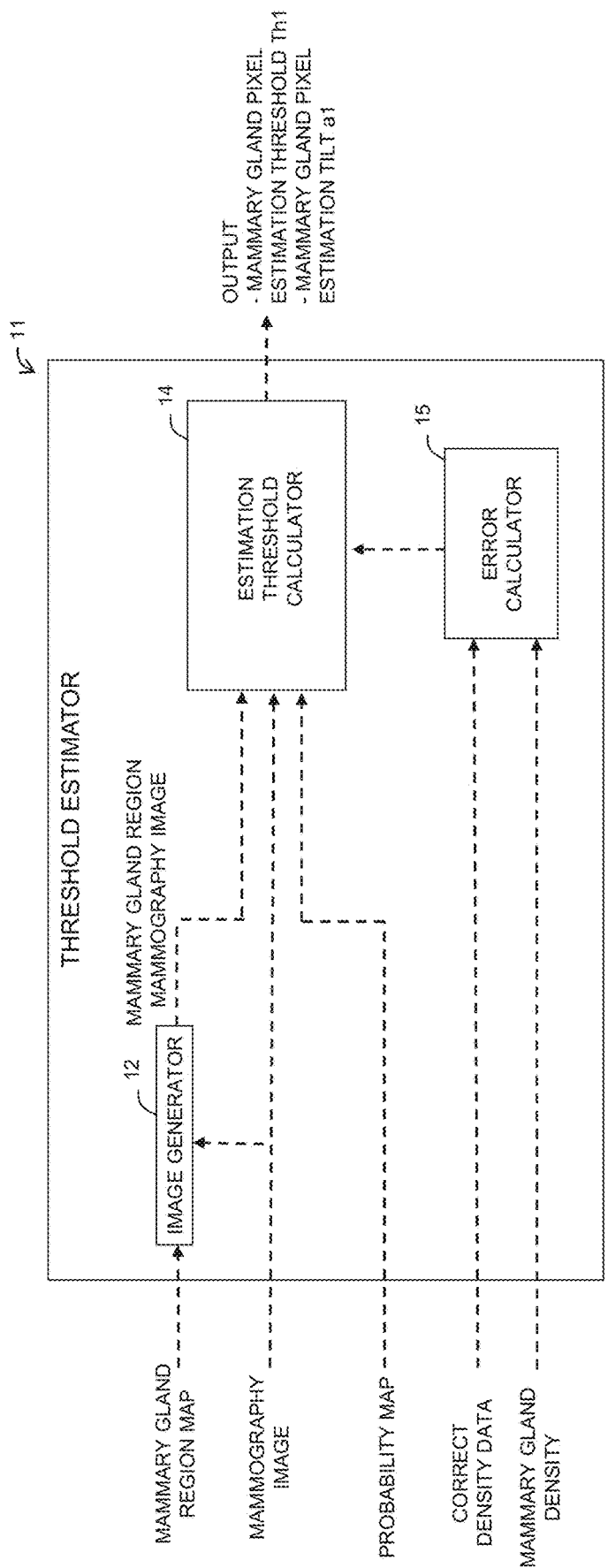
FIG. 10 a block diagram showing a configuration of a threshold estimator 11 according to modification 2 of the first embodiment.

In the embodiment, the case where the input data of the threshold estimator 11 is a histogram (first through third histograms) has been described as an example, but the present invention is not limited to this. As shown in FIG. 10, the input data for the threshold estimator 11 may be the mammography image, the mammary gland region mammography image, and the probability map. In this case, CNN (Convolutional Neural Network), which is a convolutional network, can be employed to configure the estimation threshold calculator 14 of the threshold estimator 11. In this modification 2, although the computing load of the estimation threshold calculator 14 increases compared to the embodiment, the accuracy of the calculated mammary gland pixel estimation threshold Th1, etc. is further increased, and as a result, the accuracy of the calculated mammary gland density can be expected to be further increased.

1-3-3. Modification 3: Use Correct Mammary Gland Pixel Estimation Threshold as Correct Data In the first embodiment, the case where the error calculator 15 calculates the error between the calculated mammary gland density and the correct mammary gland density (correct density data), and the estimation threshold calculator 14 learns the relationship between the mammography image (the first to third histograms in the embodiment) and the mammary gland pixel estimation threshold based on this error has been described as an example, but the present invention is not limited to this. In other words, in the learning step of the first embodiment, the case where the relationship between the mammography image and the mammary gland pixel estimation threshold is learned based on the correct mammary gland density and the calculated mammary gland density has been described as an example, but the present invention is not limited to this.

The error calculator 15 may calculate the error between the mammary gland pixel estimation threshold calculated by the estimation threshold calculator 14 and the correct mammary gland pixel estimation threshold, and the estimation threshold calculator 14 may learn the relationship between the mammography image and the mammary gland pixel estimation threshold based on this error. In other words, in the learning step, the relationship between the mammography image and the mammary gland pixel estimation threshold may be learned based on the correct mammary gland density used to calculate the correct mammary gland pixel estimation threshold described above and the mammary gland pixel estimation threshold output in the learning step.

For example, if the mammary gland pixel estimation threshold 1 is a predetermined value, and the mammary gland density (the correct mammary gland density) is acquired as the correct data, the mammary gland pixel estimation threshold can be back-calculated to become the mammary gland density. Since this back-calculated mammary gland pixel estimation threshold is the value acquired corresponding to the correct mammary gland density as the correct data, in modification 3, the back-calculated mammary gland pixel estimation threshold is referred to as the correct mammary gland pixel estimation threshold.

In modification 3, the threshold estimator 11 further has a correct data acquirer (not shown), the correct data acquirer back-calculates the correct mammary gland pixel estimation threshold based on the correct mammary gland density to acquire the correct mammary gland pixel estimation threshold. Then, the error calculator 15 calculates the error between the mammary gland pixel estimation threshold calculated by the estimation threshold calculator 14 and the correct mammary gland pixel estimation threshold acquired by the correct mammary gland pixel estimation threshold, and the estimation threshold calculator 14 learns the relationship between the mammography image and mammary gland pixel estimation threshold based on the error.

Also, the mammary gland pixel estimation threshold may be taken as a value that includes not only the threshold but also the tilt corresponding to the mammary gland pixel estimation tilt. In this case, the threshold in the mammary gland pixel estimation threshold is a predetermined value, while the tilt included in the mammary gland pixel estimation threshold is a value calculated by the estimation threshold calculator 14. Note that the correct mammary gland pixel estimation tilt can be back-calculated in the same manner as the correct mammary gland pixel estimation threshold described above. Then, the error calculator 15 calculates the error between the tilt calculated by the estimation threshold calculator 14 and the correct mammary gland pixel estimation tilt, and the estimation threshold calculator 14 learns the relationship between the mammography image and the mammary gland pixel estimation threshold that includes the tilt described above, based on this error.

2. Second Embodiment

In the second embodiment, descriptions of the configurations common to the first embodiment will be omitted as appropriate, and the descriptions will focus on the configurations that differ.

The first embodiment is a configuration in which the mammary gland pixel area La of the pixels in the mammary gland region R within the mammography image is calculated. The mammary gland pixel area La is the degree of the mammary gland pixel-likeness of the pixels in the mammary gland region R, as described in the first embodiment. By learning the relationship between the mammography image and the mammary gland pixel estimation threshold Th1 and the mammary gland pixel estimation tilt a1, the threshold estimator 11 can calculate the mammary gland pixel area La.

The second embodiment is a configuration in which the mammary gland region area Lb of each pixel in the probability map is calculated. The mammary gland region area Lb is a value that indicates the degree to which the pixel in the probability map (in the mammography image) constitutes the mammary gland region R or not. In other words, the mammary gland region area Lb is a value that indicates the degree to which a pixel in the probability map is included in the mammary gland region R or not. The pixel with a large mammary gland region area Lb is likely to be the candidate pixel, and conversely, the pixel with a small mammary gland region area Lb is unlikely to be the candidate pixel. In the second embodiment, by learning the relationship between the mammography image and the mammary gland region estimation threshold Th2 and the mammary gland region estimation tilt a2, the threshold estimator 11 can calculate the mammary gland region area Lb.

2-1. Configuration Description 2-1-1. Mammary Gland Region Extractor 3

The pre-processor 6 and the mammary gland region probability calculator 7 are the same as in the first embodiment, so they are not described.

<Post-Processor 8>

Figure 14A:
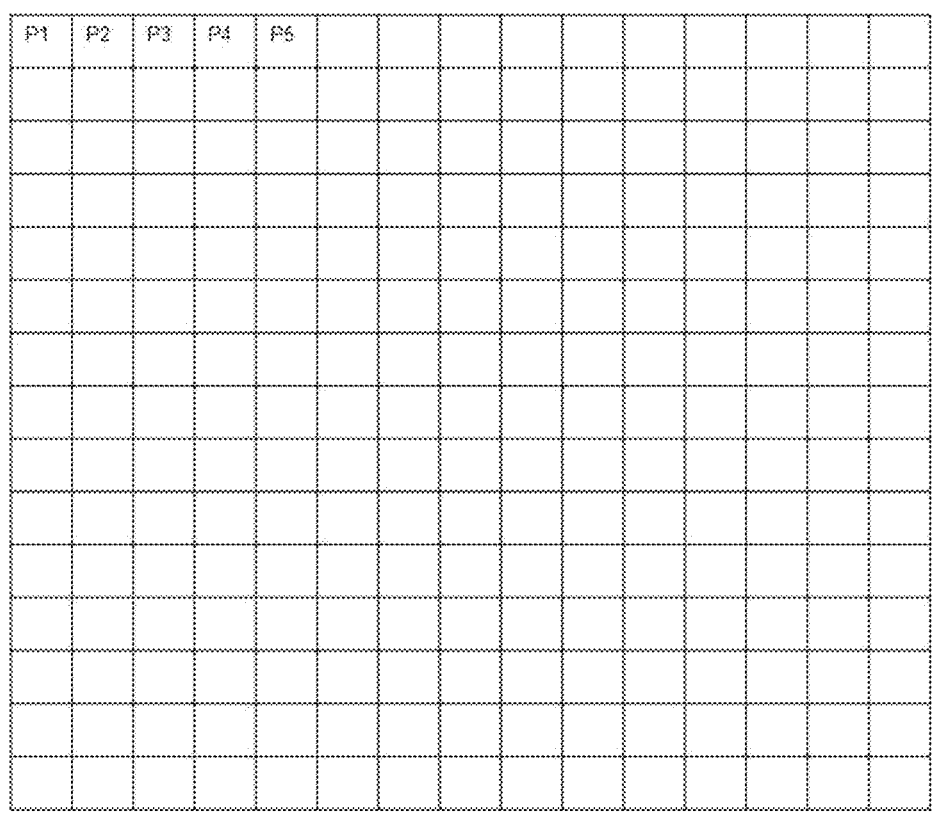
FIG. 14A is a schematic diagram of an example of a probability map.
Figure 14B:
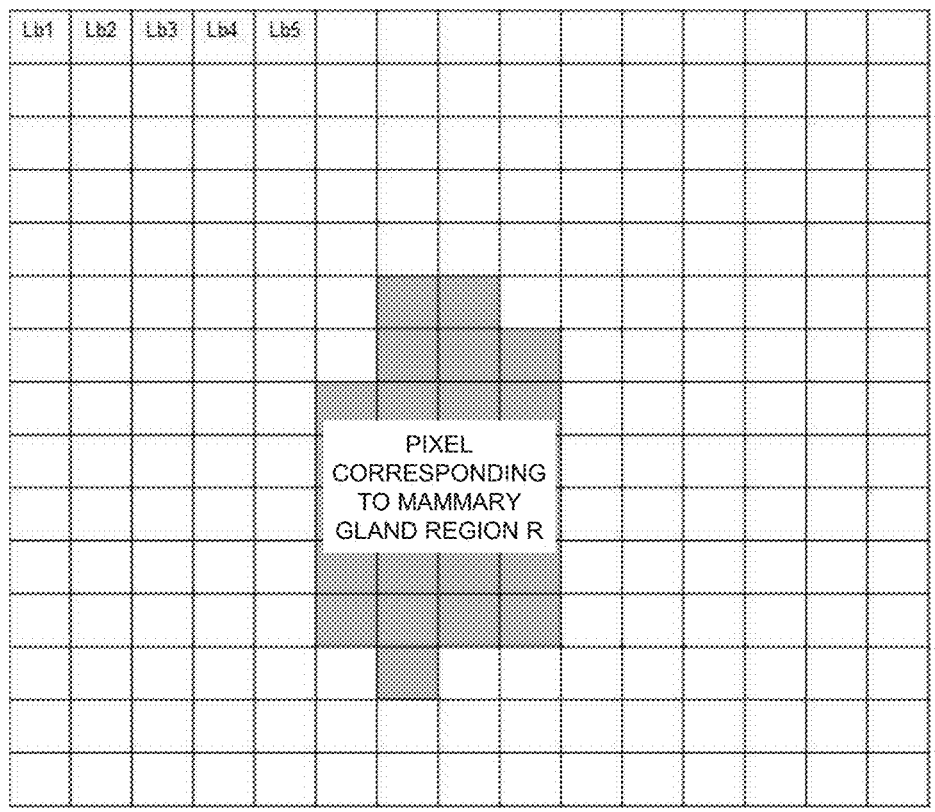
FIG. 14B is a schematic diagram of an example of a candidate pixel area map.

The post-processor 8 acquires the mammary gland region area Lb (mammary gland region area map) shown in FIG. 14B based on the probability P (probability map) shown in FIG. 14A. Then, the post-processor 8 extracts the mammary gland region R based on the mammary gland region area Lb (candidate pixel area map). The post-processor 8 has the mammary gland region area calculator 9B instead of the candidate pixel extractor 9.

Mammary Gland Region Area Calculator 9B

The mammary gland region area calculator 9B generates the mammary gland region area map shown in FIG. 14B. The mammary gland region area map is the map in which the mammary gland region area Lb has been calculated for each pixel in the probability map. In FIG. 14B, the pixel in gray in the center is a schematic illustration of the pixel corresponding to the mammary gland region R. The pixel in gray has a higher value of mammary gland region area Lb than the pixel in white.

The mammary gland region area calculator 9B performs the second pixel area calculation process for each pixel in the probability map. the second pixel area calculation process is the process of calculating the mammary gland region area Lb based on the probability P of each pixel. As shown in FIG. 14A and FIG. 14B, the second pixel area calculation process is performed for the probability P of each pixel in the probability map (only probability P1 to P5 are shown in FIG. 14A) to calculate the mammary gland region area Lb (only the mammary gland pixel area Lb1 to Lb5 are shown in FIG. 14B). The mammary gland region area Lb is calculated based on the second threshold function shown in FIG. 15.

Second Threshold Function

Figure 15:
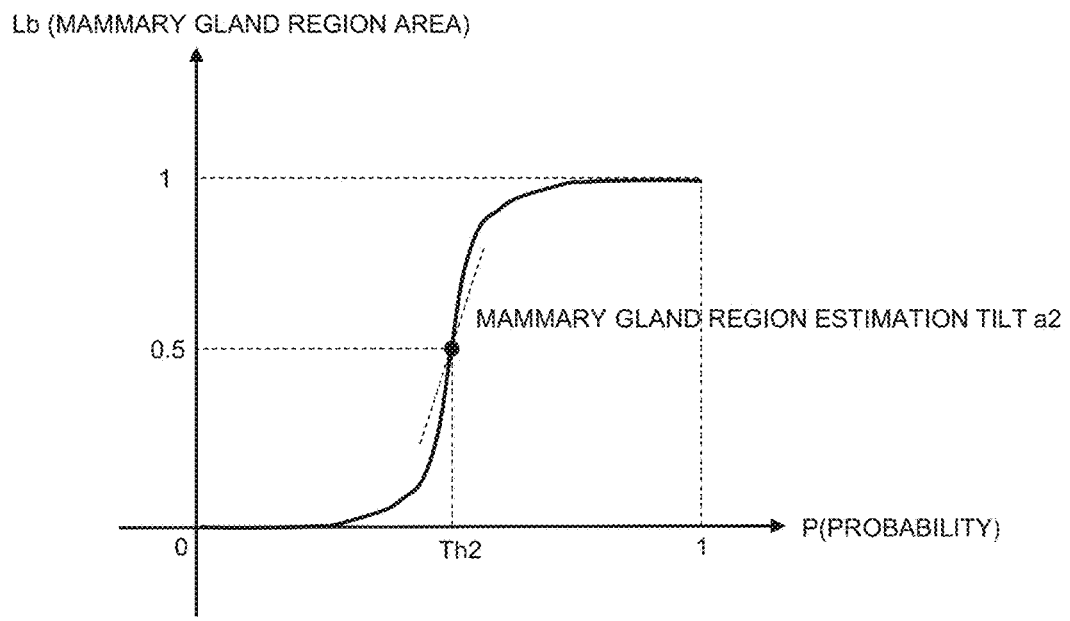
FIG. 15 is an illustration of the second threshold function (sigmoid function) that defines the relationship between the probability P and the mammary gland region area Lb of each pixel in the mammography image.

When the mammary gland region area calculator 9B calculates the mammary gland region area Lb based on the probability P, the mammary gland region area calculator 9B uses the second threshold function shown in FIG. 15. The second threshold function is the function associated with the probability P of each pixel and the mammary gland region area Lb of each pixel. Also, the second threshold function is the function that rises sharply at the mammary gland region estimation threshold Th2. That is, in the second threshold function, in the range of pixel values smaller than the mammary gland region estimation threshold Th2, the mammary gland region area Lb is 0 or close to 0, in the range of pixel values larger than the mammary gland region estimation threshold Th2, the mammary gland region area Lb is 1 or close to 1. Thus, the mammary gland region estimation threshold Th2 is the threshold in the second threshold function. In the second embodiment, the second threshold function is also a sigmoid function, but other functions can also be employed. The second threshold function (sigmoid function) of the second embodiment is represented by the formula shown in FIG. 15, and the curve shape of the second threshold function is determined by defining the mammary gland region estimation threshold Th2 and the mammary gland region estimation tilt a2. The mammary gland region estimation tilt a2 corresponds to the tilt of the second threshold function when the pixel value of the second threshold function is the mammary gland region estimation threshold Th2.

Output: Mammary Gland Region Area Lb

The mammary gland region area Lb is a value that indicates the degree to which a pixel in the probability map is included in the mammary gland region R, as described above. For example, if the mammary gland region area Lb of a given pixel is 1, the given pixel can be regarded as a candidate pixel of the mammary gland region itself, and if the mammary gland region area Lb of a given pixel is 0, the given pixel can be regarded as not being a candidate pixel. In addition, the mammary gland region area Lb can also take an intermediate value that is larger than 0 and smaller than 1.

That is, the mammary gland region area calculator 9B does not determine whether a pixel in the probability map is either a candidate pixel of the mammary gland region or not. In other words, the mammary gland region area Lb is not a value that can be used to clearly determine whether a given pixel is a candidate pixel or not. In an embodiment, the mammary gland region area Lb is calculated for each pixel of the entire mammography image.

Input: Mammary Gland Region Estimation Threshold Th2 and Mammary Gland Region Estimation Tilt a2

The mammary gland region area calculator 9B receives the mammary gland region estimation threshold Th2 and the mammary gland region estimation tilt a2 from the threshold estimator 11. Then, the mammary gland region area calculator 9B calculates the mammary gland region area Lb of the pixels in the probability map based on the probability P of the pixels in the probability map and the second threshold function to which the mammary gland region estimation threshold Th2 and the mammary gland region estimation tilt a2 are substituted. The mammary gland region estimation tilt a2 may be a fixed value or a value that can be changed by the users as appropriate.

Region Generator 10

The region generator 10 generates the mammary gland region based on the mammary gland region area map. Various methods can be used to generate the mammary gland region. The following (1) and (2) are described here as an example.

(1) For example, the mammary gland region area calculator 9B determines the pixels in the mammary gland region area map whose mammary gland region area Lb is larger than a predetermined threshold as candidate pixels as described in the first embodiment, and the region generator 10 generates a candidate pixel map. Since the mammary gland region area Lb is calculated based on the threshold function (sigmoid function in the second embodiment), most of the values of mammary gland region area Lb are 0 or close to 0, or 1 or close to 1. Therefore, if the predetermined threshold is set to a value such as 0.5, the mammary gland region area calculator 9B can properly generate a candidate pixel map.

(2) Also, the region generator 10 may also generate the mammary gland region R based on the mammary gland region area map, for example, by performing a filter process on the mammary gland region area map.

2-1-2. Mammary Gland Pixel Area Calculator 4

The mammary gland pixel area calculator 4 generates the mammary gland region area map shown in FIG. 7B. The mammary gland pixel area calculator 4 generates the mammary gland region area map using the predetermined mammary gland pixel estimation threshold Th1 and the mammary gland pixel estimation tilt a1. That is, in the first embodiment, the mammary gland pixel area calculator 4 acquires the mammary gland pixel estimation threshold Th1 and the mammary gland pixel estimation tilt a1 from the threshold estimator 11, but in the second embodiment, it is a predetermined value. The mammary gland pixel estimation threshold Th1 and the mammary gland pixel estimation tilt a1 may be a fixed value or a value that can be changed by the users as appropriate.

The mammary gland pixel area calculator 4 acquires the mammary gland region map from the post-processor 8. Then, the mammary gland pixel area calculator 4 performs the first pixel area calculation process for the pixels in the mammary gland region R. That is, the mammary gland pixel area calculator 4 calculates the mammary gland pixel area La based on the pixel values of the pixels in the mammary gland region R and the first threshold function to which the mammary gland pixel estimation threshold Th1 and the mammary gland pixel estimation tilt a1 are substituted.

2-1-3. Mammary Gland Density Calculator 5

The method of calculating the mammary gland density is the same as the first embodiment. The mammary gland density calculator 5 calculates the mammary gland density based on the sum of the mammary gland pixel area La of all pixels in the mammary gland region R. More specifically, the mammary gland density calculator 5 calculates the sum of the mammary gland pixel area La of all pixels in the mammary gland region R and the number of all pixels in the mammary gland region R, and the mammary gland density is calculated based on the following formula.

mammary gland density (%)=100×(sum of mammary gland pixel area $La$)/(total number of pixels in mammary gland region)

In the second embodiment, the mammary gland region map of the post-processor 8 is output to the mammary gland pixel area calculator 4, the mammary gland pixel area calculator 4 generates the mammary gland pixel area map based on the mammary gland region map, and the mammary gland density calculator 5 calculates the mammary gland density based on the mammary gland pixel area map.

2-1-4. Threshold Estimator 11

In the learning phase and the operation phase, the threshold estimator 11 has the function of calculating the mammary gland region estimation threshold Th2 and mammary gland region estimation tilt a2 based on the mammography image, etc.

<Estimation Threshold Calculator 14>

In the learning phase, the estimation threshold calculator 14 has the function of learning the relationship between the mammography image and the values related to the second threshold function (mammary gland region estimation threshold Th2 and mammary gland region estimation tilt a2). In the second embodiment, the estimation threshold calculator 14 uses the probability map generated from the mammography image and the mammary gland region mammography image generated from the mammography image in addition to the mammography image for learning.

Figure 11:
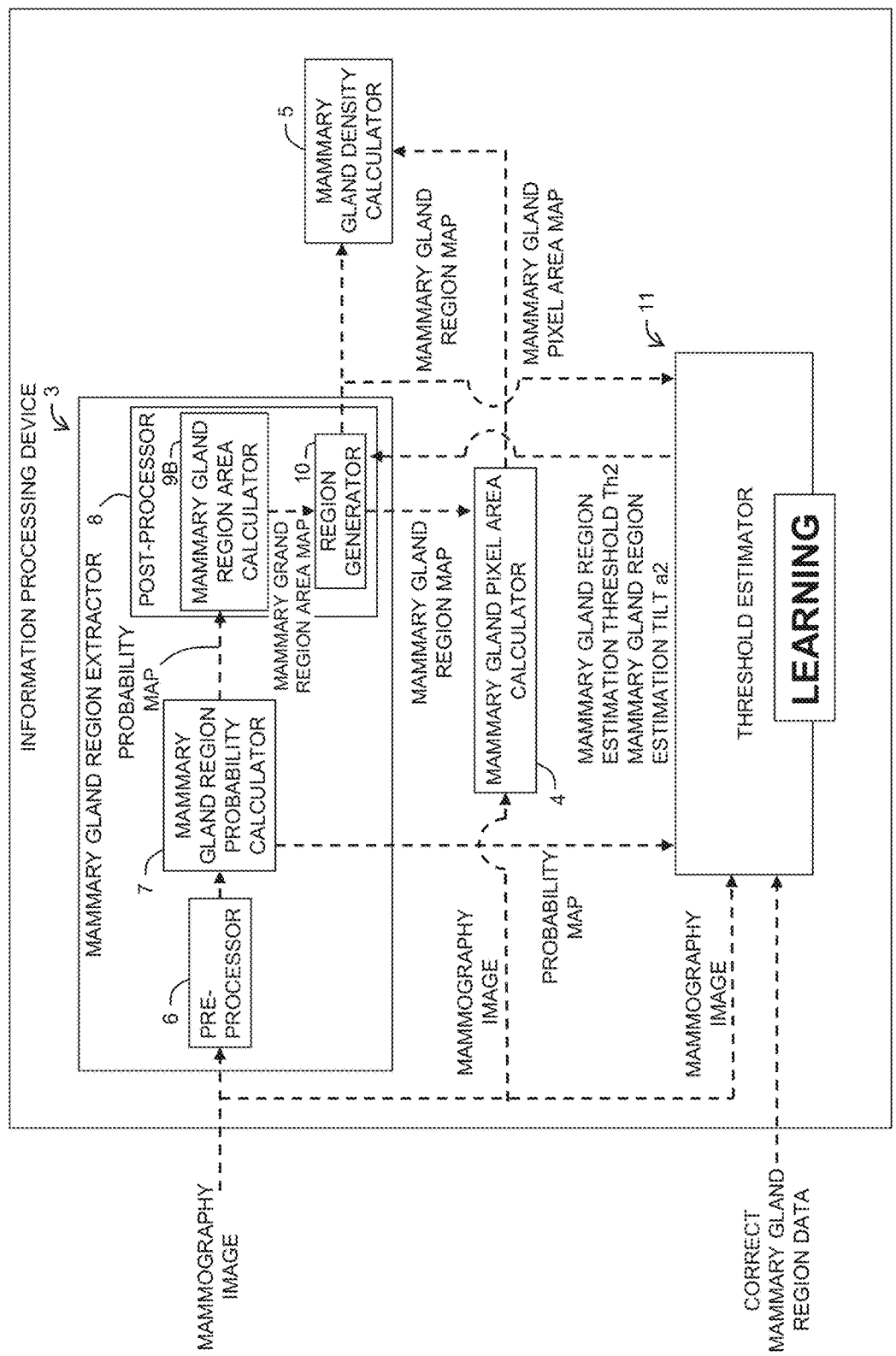
FIG. 11 is a block diagram showing a configuration of an information processing device 1 according to the second embodiment and a flow of various data in the learning phase.

When the mammography image is input, the estimation threshold calculator 14 learns based on the learning model that outputs the mammary gland region estimation threshold Th2 and mammary gland region estimation tilt a2. Also, the filter weight coefficients of the neural network of the estimation threshold calculator 14 are updated accordingly based on the error calculated by the error calculator 15. As shown in FIG. 11 and FIG. 13, when the estimation threshold calculator 14 outputs the mammary gland region estimation threshold Th2 and mammary gland region estimation tilt a2, the post-processor 8 calculates the mammary gland region area Lb based on the second threshold function and generates the mammary gland region area map, furthermore, the post-processor 8 generates the mammary gland region map based on the mammary gland region area map. The generated mammary gland region map is output to the threshold estimator 11 and compared with the correct mammary gland region data described below. Then, the estimation threshold calculator 14 receives the difference (error) between the mammary gland region map generated by the post-processor 8 and the correct mammary gland region data from the error calculator 15. This allows the filter weight coefficients of the neural network of the estimation threshold calculator 14 to be updated accordingly based on this error.

<Error Calculator 15>

The error calculator 15 compares the correct mammary gland region data (the correct mammary gland region) input to the information processing device 1 with the mammary gland region map generated by the post-processor 8. Here, the correct mammary gland region data is the correct data in which the mammary gland region has been determined by a doctor or other person. In other words, the correct mammary gland region data is determined to be the mammary gland region by visually examining the corresponding mammography image by a doctor or other person. The error calculator 15 outputs the calculated difference (error) to the estimation threshold calculator 14.

2-2. Operational Description
2-2-1. Learning Phase

The operation in the learning phase of the mammary gland region estimation threshold Th2 is described with reference to FIG. 11 and FIG. 13.

The learning method of the second embodiment includes an acquiring step, a probability map generating step, the mammary gland region extracting step, an image generating step, a histogram generating step, a learning step, a mammary gland pixel area map generating step, and a mammary gland density acquiring step.

In the acquiring step, the information processing device 1 acquires the mammography image. In the acquiring step, the mammary gland region extractor 3, the mammary gland pixel area calculator 4 and the threshold estimator 11 receive the mammography image. Also, in the acquiring step, the information processing device 1 acquires the correct mammary gland region data. In addition, in the acquiring step, the error calculator 15 receives the correct mammary gland region data.

In the probability map generating step, the mammary gland region probability calculator 7 generates the probability map based on the mammography image that has been pre-processed. The mammary gland region probability calculator 7 outputs the probability map to the post-processor 8 and the threshold estimator 11.

The mammary gland region extracting step includes the mammary gland region area map generating step and the mammary gland region map generating step. In the mammary gland region area map generating step, the post-processor 8 generates the mammary gland region area map based on the probability map. Then, in the mammary gland region map generating step, the post-processor 8 generates the mammary gland region map based on the mammary gland region area map, the post-processor 8 outputs the mammary gland region map to the mammary gland pixel area calculator 4 and the threshold estimator 11.

In the image generating step, the image generator 12 generates the mammary gland region mammography image based on the mammography image acquired in the acquiring step.

In the histogram generating step, the histogram generator 13 generates the first through third histograms based on the mammography image. More specially, in the histogram generating step, the histogram generator 13 generates the first through third histograms based on the mammography image acquired in the acquiring step, the mammary gland region mammography image generated in the image generating step, and the probability map generated in the probability map generating step. The histogram generator 13 outputs the first through third histograms to the estimation threshold calculator 14.

In the learning step, the estimation threshold calculator 14 learns a relationship between the mammography image and the mammary gland region estimation threshold Th2. More specifically, the estimation threshold calculator 14 learns the relationship between the mammography image and the mammary gland region estimation threshold Th2, and the relationship between the mammography image and the mammary gland region estimation tilt a2, because the mammary gland region estimation tilt a2 is also a learning target in the second embodiment.

In the learning step, the error calculated by the error calculator 15 is input to the estimation threshold calculator 14. This error corresponds to the difference between the mammary gland region map generated in the mammary gland region map generating step and the correct mammary gland region data. As a result, the weight coefficients of the filters of the estimation threshold calculator 14 are updated accordingly, and the accuracy of the output of the estimation threshold calculator 14 (the mammary gland region estimation threshold Th2 and the mammary gland region estimation tilt a2) will be increased. In other words, the mammary gland region map generated by the post-processor 8 is calculated based on the mammary gland region estimation threshold Th2, etc., the mammary gland region map generated by the post-processor 8 is compared with the correct mammary gland region data as the correct data, and the weight coefficient of the filter of the estimation threshold calculator 14 is updated accordingly. From the above, in the learning step, the estimation threshold calculator 14 learns the relationship between the mammography image and the mammary gland region estimation threshold Th2, and can calculate a more objective mammary gland region estimation threshold Th2.

In the mammary gland pixel area map generating step, the mammary gland pixel area calculator 4 generates the mammary gland pixel area map based on the mammography image acquired in the acquiring step, the mammary gland region map acquired from the post-processor 8 and the first threshold function to which the mammary gland pixel estimation threshold Th1 and the mammary gland pixel estimation tilt a1 are substituted.

In the mammary gland density acquiring step, the mammary gland density calculator 5 calculates the mammary gland density based on the mammary gland pixel area map.

2-2-2. Operational Phase

Figure 12:
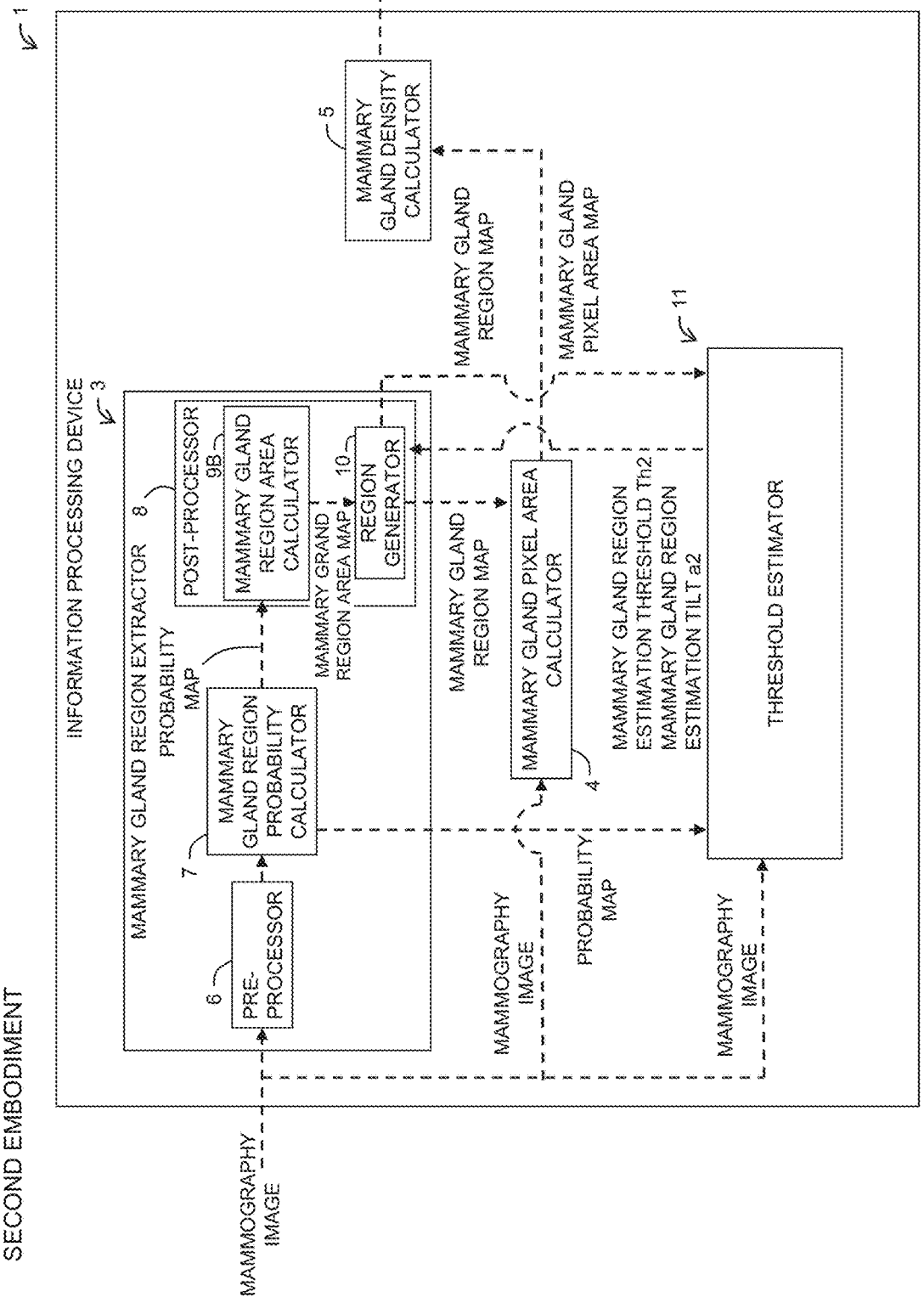
FIG. 12 is a flow of various data in the operational phase with reference to the block diagram shown in FIG. 11.

The operation in the operational phase is described based on FIG. 12. This section describes the operation in the operational phase, which differs from the operation in the learning phase.

The operational method of the second embodiment (the acquisition method of the mammary gland density) includes the acquiring step, the probability map generating step, the mammary gland region extracting step, the image generating step, the histogram generating step, the threshold and tilt calculating step, the mammary gland pixel area map generating step and the mammary gland density acquiring step.

The probability map generating step, the mammary gland region extracting step, the mammary gland region extracting step, the image generating step, the histogram generating step, the mammary gland pixel area map generating step, and the mammary gland density acquiring step are the same as in the learning phase.

The operational phase has a threshold and tilt calculating step instead of the learning step.

In the acquiring step, the information processing device 1 does not acquire the correct mammary gland region data.

In the operational phase, the weight coefficients of the filters in the estimation threshold calculator 14 are fixed. That is, the error calculator 15 does not calculate the error, so the estimation threshold calculator 14 does not acquire the error from the error calculator 15. In the learning step, the estimation threshold calculator 14 outputs the mammary gland region estimation threshold Th2 and the mammary gland region estimation tilt a2 when the first through third histograms are input.

In the operational phase, the information processing device 1 displays the mammary gland density acquired in the mammary gland density acquiring step on the display of the information processing device 1 or output it from the information processing device 1 to an external device.

The configurations of the modifications 1 through 3 of the first embodiment can be applied to the second embodiment.

3. Third Embodiment

As shown in FIGS. 16 and 17, the configurations of the first and second embodiments may be combined. In other words, the estimation threshold calculator 14 may be configured to learn the mammary gland pixel estimation threshold Th1 and the mammary gland pixel estimation tilt a1 and to learn the mammary gland region estimation threshold Th2 and the mammary gland region estimation tilt a2. In this case, as shown in FIG. 17, the error calculator 15 calculates the first error, which is the error between the mammary gland density calculated by the mammary gland density calculator 5 and the correct density data, and the second error, which is the error between the mammary gland region map generated by the post-processor 8 and the correct mammary gland region data. Then, the filter weight coefficients of the neural network of the estimation threshold calculator 14 are updated accordingly based on the first and second errors calculated by the error calculator 15.

REFERENCE SIGNS LIST

1: information processing device
3: mammary gland region extractor
4: mammary gland pixel area calculator
5: mammary gland density calculator
6: pre-processor
7: mammary gland region probability calculator
8: post-processor
9: candidate pixel extractor
9B: mammary gland region area calculator
10: region generator
11: threshold estimator
12: image generator
13: histogram generator
14: estimation threshold calculator
15: error calculator
B: breast region
G: pectoralis major muscle region
La: mammary gland pixel area
Lb: mammary gland region area
P: probability
R: mammary gland region
Th1: mammary gland pixel estimation threshold
Th2: mammary gland region estimation threshold
a1: mammary gland pixel estimation tilt
a2: mammary gland region estimation tilt

The invention claimed is:

1. A method for learning a threshold value applied to pixels in a mammography image comprising:
an acquiring step; a histogram generation step; and a learning step, wherein
in the acquiring step, the mammography image is acquired,
in the histogram generation step, first to third histograms are generated,
the first histogram is a histogram of a pixel value of each pixel in the mammography image,
the second histogram is a histogram of a pixel value of each pixel in a mammary gland region in the mammography image, and
the third histogram is a histogram of a mammary gland region probability of each pixel in the mammography image,
the mammary gland region probability indicates a probability that each pixel in the mammography image is in the mammary gland region,
in the learning step, a relationship between the first to third histograms and a mammary gland pixel estimation threshold is learned,
the mammary gland pixel estimation threshold is a threshold value used to calculate a mammary gland pixel area of each pixel of the mammary gland region in the mammography image, and
the mammary gland pixel area is a value indicating a degree of a mammary gland pixel-likeness of the pixel in the mammography image.

2. The method of claim 1 further comprising a mammary gland density acquiring step, wherein
in the acquiring step, a correct mammary gland density in the mammary gland region is further acquired,
in the mammary gland density acquiring step, a calculated mammary gland density in the mammary gland region is acquired based on the mammography image and the mammary gland pixel estimation threshold,
in the learning step, the relationship is learned based on the correct mammary gland density, and the calculated mammary gland density or the mammary gland pixel estimation threshold output in the learning step.

3. The method of claim 2, wherein
in the learning step, a relationship between the mammography image and a mammary gland pixel estimation tilt is further learned,
the mammary gland pixel estimation threshold is a threshold of a predetermined threshold function,
the mammary gland pixel estimation tilt is a tilt of the threshold function at the mammary gland pixel estimation threshold,
the threshold function is a function that associates a pixel value of each pixel in the mammary gland region with the mammary gland pixel area of each such pixel, and
in the mammary gland density acquiring step, the mammary gland pixel area of each pixel in the mammary gland region is calculated based on the threshold function, the mammary gland pixel estimation threshold, and the mammary gland pixel estimation tilt, and the calculated mammary gland density is acquired based on the sum of the mammary gland pixel area.

4. The method of claim 1, wherein
the mammary gland region is a narrower region than an entire breast in the mammography image.

5. A method for learning a threshold value applied to pixels in a mammography image comprising:
an acquiring step; and a learning step, wherein
in the acquiring step, the mammography image is acquired,
in the learning step, a relationship between the mammography image and a mammary gland pixel estimation threshold is learned,
the mammary gland pixel estimation threshold is a threshold value used to calculate a mammary gland pixel area of each pixel of a mammary gland region in the mammography image, and
the mammary gland pixel area is a value indicating a degree of a mammary gland pixel-likeness of the pixel in the mammography image,
the method further comprising a mammary gland density acquiring step, wherein
in the acquiring step, a correct mammary gland density in the mammary gland region is further acquired,
in the mammary gland density acquiring step, a calculated mammary gland density in the mammary gland region is acquired based on the mammography image and the mammary gland pixel estimation threshold, in the learning step, the relationship is learned based on the correct mammary gland density, and the calculated mammary gland density or the mammary gland pixel estimation threshold output in the learning step, in the learning step, a relationship between the mammography image and a mammary gland pixel estimation tilt is further learned, the mammary gland pixel estimation threshold is a threshold of a predetermined threshold function, the mammary gland pixel estimation tilt is a tilt of the threshold function at the mammary gland pixel estimation threshold, the threshold function is a function that associates a pixel value of each pixel in the mammary gland region with the mammary gland pixel area of each such pixel, and in the mammary gland density acquiring step, the mammary gland pixel area of each pixel in the mammary gland region is calculated based on the threshold function, the mammary gland pixel estimation threshold, and the mammary gland pixel estimation tilt, and the calculated mammary gland density is acquired based on the sum of the mammary gland pixel area.

6. The method of claim 5, wherein
the mammary gland region is a narrower region than an entire breast in the mammography image.

* * * * *